United States Patent
Beausoleil et al.

(10) Patent No.: US 10,981,892 B2
(45) Date of Patent: *Apr. 20, 2021

(54) ACYL SULFONAMIDES THAT ARE BCL FAMILY ANTAGONISTS FOR USE IN CLINICAL MANAGEMENT OF CONDITIONS CAUSED OR MEDIATED BY SENESCENT CELLS AND FOR TREATING CANCER

(71) Applicant: Unity Biotechnology, Inc., South San Francisco, CA (US)

(72) Inventors: Anne-Marie Beausoleil, South San Francisco, CA (US); Ryan Hudson, South San Francisco, CA (US)

(73) Assignee: Unity Biotechnology, Inc., South San Francisco, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/897,905

(22) Filed: Jun. 10, 2020

(65) Prior Publication Data

US 2020/0317640 A1 Oct. 8, 2020

Related U.S. Application Data

(63) Continuation of application No. 16/888,197, filed on May 29, 2020, which is a continuation of application No. 16/446,360, filed on Jun. 19, 2019, now Pat. No. 10,717,722, which is a continuation of application No. PCT/US2019/037067, filed on Jun. 13, 2019.

(60) Provisional application No. 62/684,681, filed on Jun. 13, 2018.

(51) Int. Cl.
| | |
|---|---|
| *C07F 9/6509* | (2006.01) |
| *C07D 401/12* | (2006.01) |
| *A61P 11/00* | (2006.01) |
| *A61P 9/10* | (2006.01) |
| *A61P 27/00* | (2006.01) |
| *A61P 35/00* | (2006.01) |
| *C07D 401/10* | (2006.01) |
| *C07D 401/14* | (2006.01) |
| *C07D 403/10* | (2006.01) |

(52) U.S. Cl.
CPC ............ *C07D 401/12* (2013.01); *A61P 9/10* (2018.01); *A61P 11/00* (2018.01); *A61P 27/00* (2018.01); *A61P 35/00* (2018.01); *C07D 401/10* (2013.01); *C07D 401/14* (2013.01); *C07D 403/10* (2013.01); *C07F 9/650952* (2013.01)

(58) Field of Classification Search
CPC .............. C07D 401/12; C07F 9/650952
See application file for complete search history.

(56) References Cited

U.S. PATENT DOCUMENTS

| | | | |
|---|---|---|---|
| 8,563,735 B2 | 10/2013 | Bruncko et al. | |
| 8,691,184 B2* | 4/2014 | Wang | C07D 231/12 424/1.11 |
| 9,096,625 B2* | 8/2015 | Wang | A61K 45/06 |
| 9,248,140 B2 | 2/2016 | Diebold et al. | |
| 9,403,856 B2 | 8/2016 | Wang et al. | |
| 9,849,128 B2 | 12/2017 | Laberge et al. | |
| 9,901,080 B2 | 2/2018 | Campisi et al. | |
| 9,968,076 B2 | 5/2018 | Kirkland et al. | |
| 10,010,546 B2 | 7/2018 | Laberge et al. | |
| 10,195,213 B2 | 2/2019 | David | |
| 10,588,916 B2 | 3/2020 | Tsuruda et al. | |
| 2016/0122758 A1 | 5/2016 | Krizhanovsky et al. | |
| 2017/0056421 A1 | 3/2017 | Zhou et al. | |
| 2017/0216286 A1 | 8/2017 | Kirkland et al. | |
| 2017/0266211 A1* | 9/2017 | David | A61P 37/00 |
| 2018/0000816 A1 | 1/2018 | David et al. | |
| 2019/0151337 A1 | 5/2019 | Tsuruda et al. | |

FOREIGN PATENT DOCUMENTS

| | | |
|---|---|---|
| EP | 3441069 | 2/2019 |
| WO | WO 2012103059 | 8/2012 |
| WO | WO 2014113413 | 7/2014 |
| WO | WO 2016127135 | 8/2016 |
| WO | WO 2019033122 | 2/2019 |

OTHER PUBLICATIONS

Baar, et al. (2017) "Targeted Apoptosis of Senescent Cells Restores Tissue Homeostasis in Response to Chemotoxicity and Aging",Cell e16.169(1): 132-147.
Bai, et al. (1967) "BM-1197: A Novel and Specific Bcl-2/Bcl-xL Inhibitor Inducing Complete and Long-Lasting Tumor Regression In Vivo", PLoS One 9(6): e99404 pp. 1-13.
Bajwa, et al. (2012) "Inhibitors of the Anti-Apoptotic Bcl-2 Proteins: A Patent Review", Expert Opin Ther Pat. 22(1): 37-55.
Baker, et al. (2016) "Naturally Occurring p16Ink4a-Positive Cells Shorten Healthy Lifespan", Nature. Author Manuscript 530(7589): 184-189.
Blagosklonny (2013) "Selective Anti-Cancer Agents as Anti-Aging Drugs", Cancer Biology & Therapy 14(12): 1092-1097.
Campisi and Robert (2014) "Cell Senescence, Role in Aging and Age-Related Diseases", Interdiscip Top Gerontol. 39: 45-61.
Childs et al (2017) "Senescent Cells: An Emerging Target for Diseases of Ageing", Nat Rev Drug Discov. 16(10): 718-735.
Jeon, et al. (2017) "Local Clearance of Senescent Cells Attenuates the Development of Post-Traumatic Osteoarthritis and Creates a Pro-Regenerative Environment", Nature Medicine 775-781.

(Continued)

Primary Examiner — Emily A Bernhardt
(74) Attorney, Agent, or Firm — Rudy J. Ng; Bozicevic, Field & Francis llp

(57) ABSTRACT

The aryl sulfonamide compounds of this invention have powerful and cell-type specific Bcl inhibitory activity. Selected compounds in this class promote apoptosis in senescent cells, and are being developed for treating senescent-related conditions. Selected compounds in this class promote apoptosis in cancer cells, and can be developed as chemotherapeutic agents.

1 Claim, 6 Drawing Sheets

(56) References Cited

OTHER PUBLICATIONS

Figure 1:
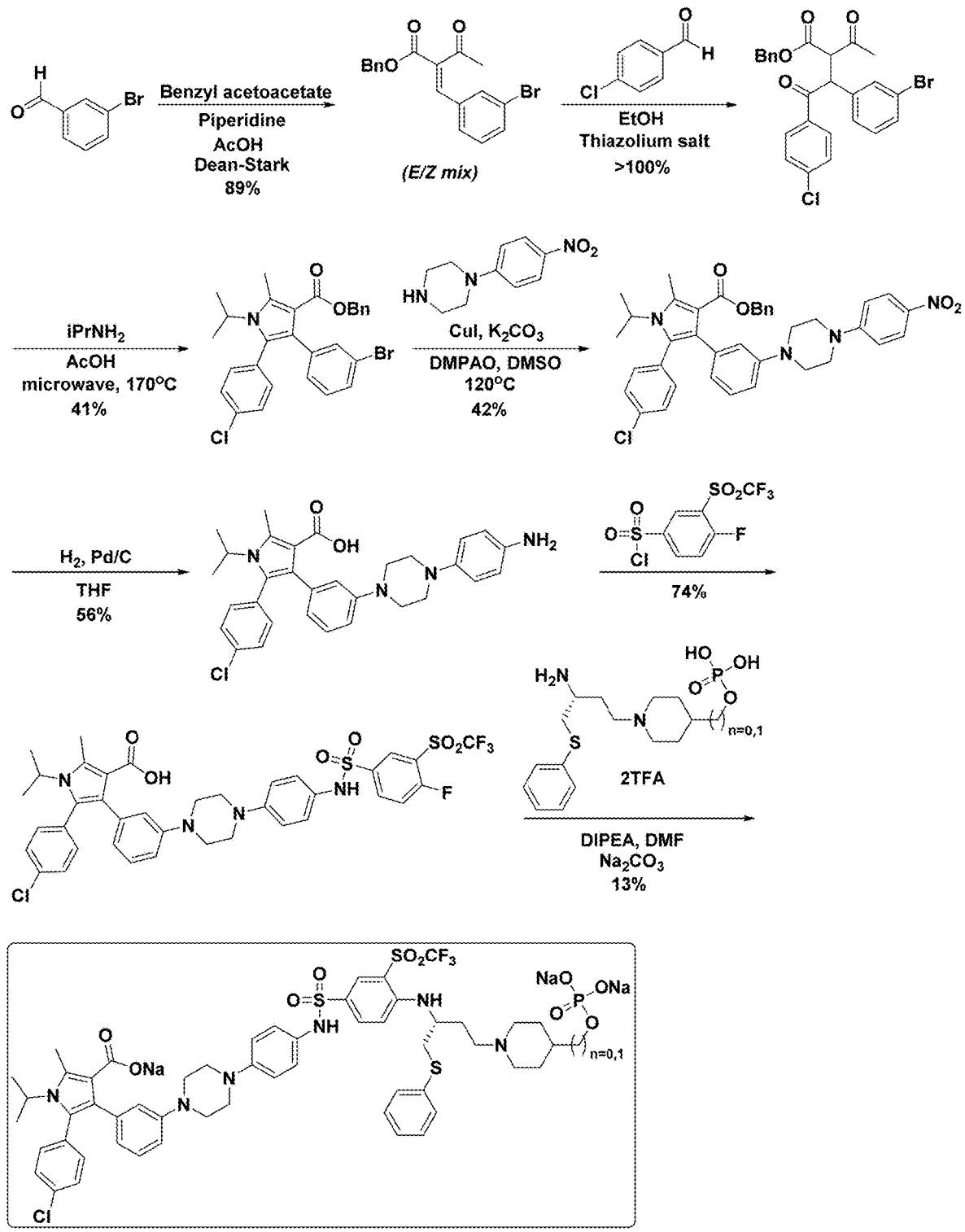

Kirkland* and Tchkonia (2015) "Clinical Strategies and Animal Models for Developing Senolytic Agents", Exp Gerontol. 68: 19-25.
Yosef, et al. (2016) "Directed Elimination of Senescent Cells by Inhibition of BCL-W and BCL-XL", Nature Communications 7:11190 pp. 1-11.
Zhu, et al. (2017) "New Agents that Target Senescent Cells: The Flavone, Fisetin, and the BCL-XL Inhibitors, A1331852 and A1155463", Aging Advance. 9 (3):955-963.
Prattichizzo et al., (2019) "Ageing as a druggable process: Moving forward" EBioMedicine, 40: 15-16.
Van Deursen et al., (2014) "The role of senescent cells in ageing" Nature, 509 (7501): 439-446.
Zhu et al., (2016) "Identification of novel senolytic agent, navitoclax, targeting the Bcl-2 family of antiapoptotic factors" Aging Cell, 15(3): 428-435.

* cited by examiner

FIG. 3A
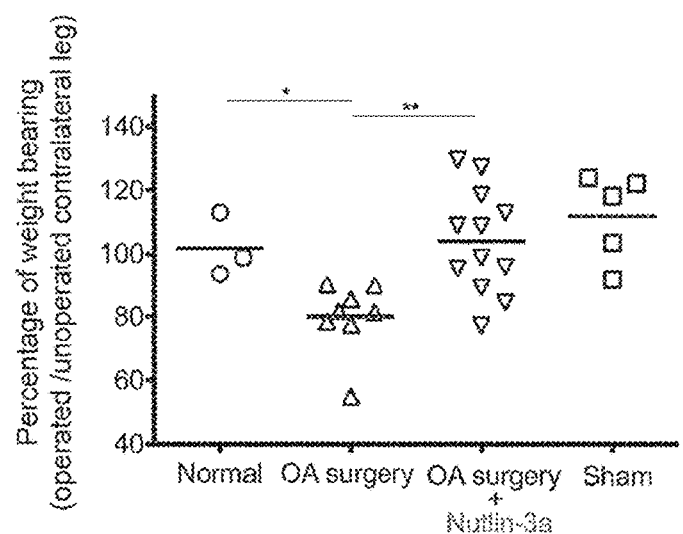
FIG. 3B
FIG. 3C
FIG. 3D
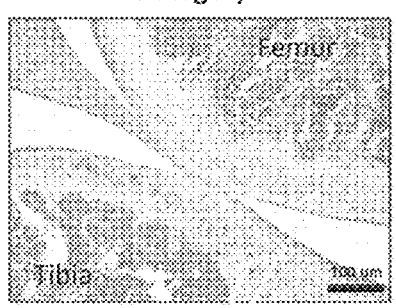
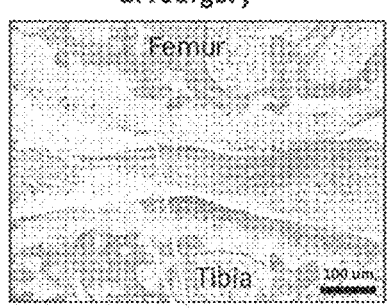
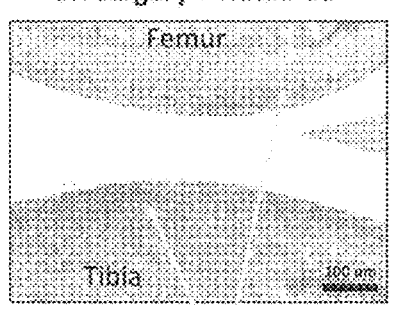

ACYL SULFONAMIDES THAT ARE BCL FAMILY ANTAGONISTS FOR USE IN CLINICAL MANAGEMENT OF CONDITIONS CAUSED OR MEDIATED BY SENESCENT CELLS AND FOR TREATING CANCER

PRIORITY APPLICATION

This application is a continuation of U.S. application Ser. No. 16/888,197, filed May 29, 2020, which is a continuation of U.S. application Ser. No. 16/446,360, filed Jun. 19, 2019, which is a continuation of international patent application PCT/US2019/037067, filed Jun. 13, 2019, which claims priority to U.S. provisional patent application No. 62/684, 681, filed Jun. 13, 2018. The disclosures of the above listed applications are hereby incorporated herein by reference in their entirety for all purposes.

FIELD OF THE INVENTION

The technology disclosed and claimed below relates generally to the field of senescent cells and their role in age-related conditions. In particular, this disclosure provides new small-molecule compounds that inhibit Bcl protein activity.

BACKGROUND

Senescent cells are characterized as cells that no longer have replicative capacity, but remain in the tissue of origin, eliciting a senescence-associated secretory phenotype (SASP). It is a premise of this disclosure that many age-related conditions are mediated by senescent cells, and that selective removal of the cells from tissues at or around the condition can be used clinically for the treatment of such conditions.

U.S. Pat. No. 10,130,628 (Laberge et al.) describes treatment of certain age-related conditions thought to be mediated at least in part by senescent cells using MDM2 inhibitors, Bcl inhibitors, and Akt inhibitors. US 20170266211 A1 (David et al.) describes the use of particular Bcl inhibitors for treatment of age-related conditions. U.S. Pat. Nos. 8,691,184, 9,096,625, and 9,403,856 (Wang et al.) describe Bcl inhibitors in a small-molecule library.

Other disclosures related to the role of senescent cells in human disease include the pre-grant publications US 2017/0056421 A1 (Zhou et al.), WO 2016/185481 (Yeda Inst.), US 2017/0216286 A1 (Kirkland et al.), and US 2017/0281649 A1 (David); and the articles by Furhmann-Stroissnigg et al. (Nat Commun. 2017 Sep. 4; 8(1):422), Blagosklonny (Cancer Biol Ther. 2013 December; 14(12): 1092-7), and Zhu et al. (Aging Cell. 2015 August; 14(4): 644-58).

SUMMARY

The disclosure that follows outlines a strategy for selectively eliminating senescent cells, and provides effective compounds, pharmaceutical compositions, development strategies, and treatment protocols, and describes many of the ensuing benefits.

A new family of Bcl inhibitors has been developed. Some of the Bcl inhibitors in this family are particularly effective senolytic agents. Contacting senescent cells in vitro or in vivo with the compounds and compositions of this disclosure selectively modulates or eliminates such cells. The inhibitors can be used for administration to a target tissue in a subject having an age-related condition, thereby selectively eliminating senescent cells in or around the tissue and relieving one or more symptoms or signs of the conditions. Alternatively or in addition, selected compounds from the family can be formulated and marketed as chemotherapeutic agents.

The invention is put forth in the description that follows, in the figures, and in the appended claims.

DRAWINGS

FIG. 1 shows a general synthetic scheme for chemically synthesizing exemplary compounds according to this invention.

Figure 2A:
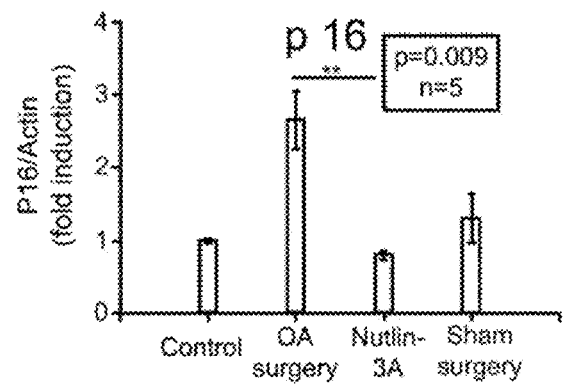
Figure 2B:
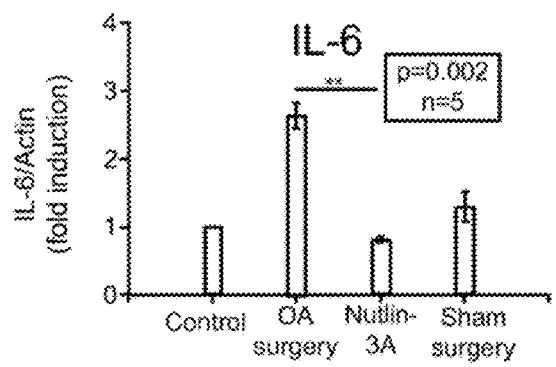
Figure 2C:
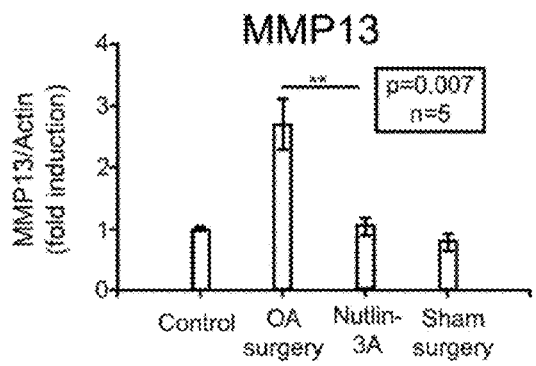

FIGS. 2A, 2B, and 2C show expression of senescent cell markers p16, IL-6, and MMP13 respectively in an osteoarthritis animal model. The senescence phenotype can be ameliorated by Nutlin-3A, a senolytic agent that inhibits MDM2. Bcl inhibitors according to this invention can be selected as senolytic agents for the same purpose.

FIG. 3A shows that an effective senolytic agent restores symmetrical weight bearing to treated mice in the osteoarthritis model. FIGS. 3B, 3C, and 3D are images showing histopathology of the joints in these mice. Treatment with the agent helps prevent or reverses destruction of the proteoglycan layer.

Figure 4A:
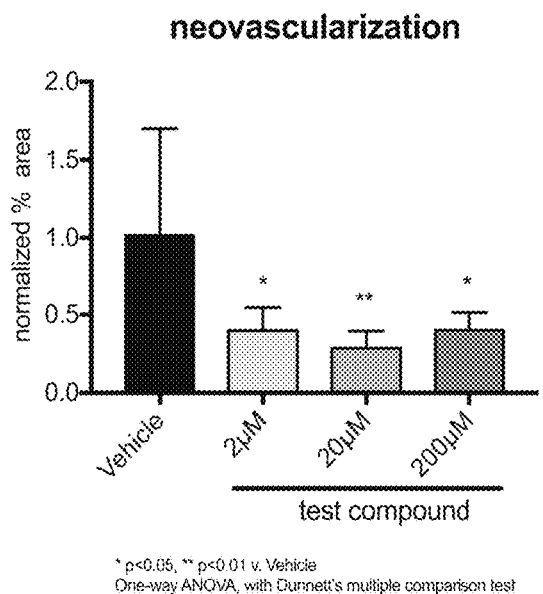
Figure 4B:
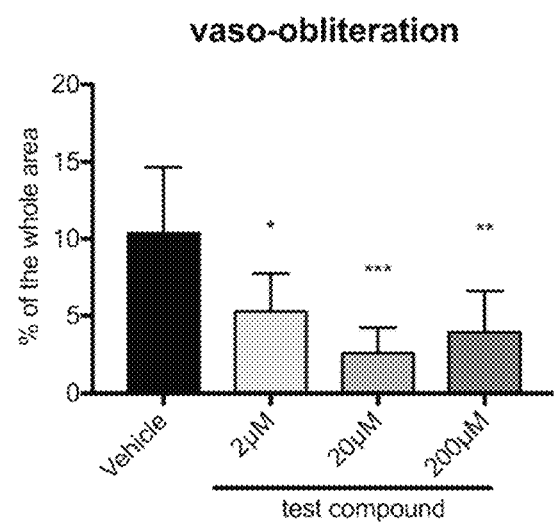
Figure 4C:
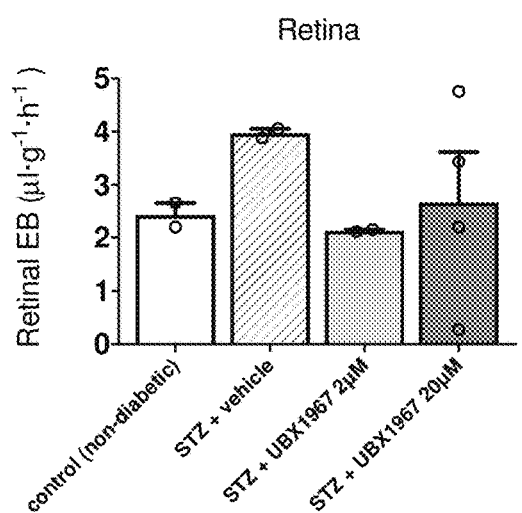
Figure 4D:
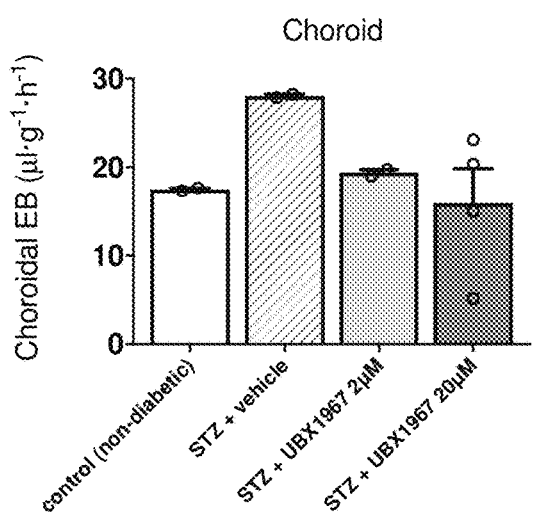

FIGS. 4A and 4B show reversal of both neovascularization and vaso-obliteration in the mouse oxygen-induced retinopathy (OIR) model when intravitreally administered with a senolytic agent. FIGS. 4C and 4D are taken from the streptozotocin (STZ) model for diabetic retinopathy. STZ-induced vascular leakage is attenuated with the intravitreal administration of a senolytic agent.

Figure 5:
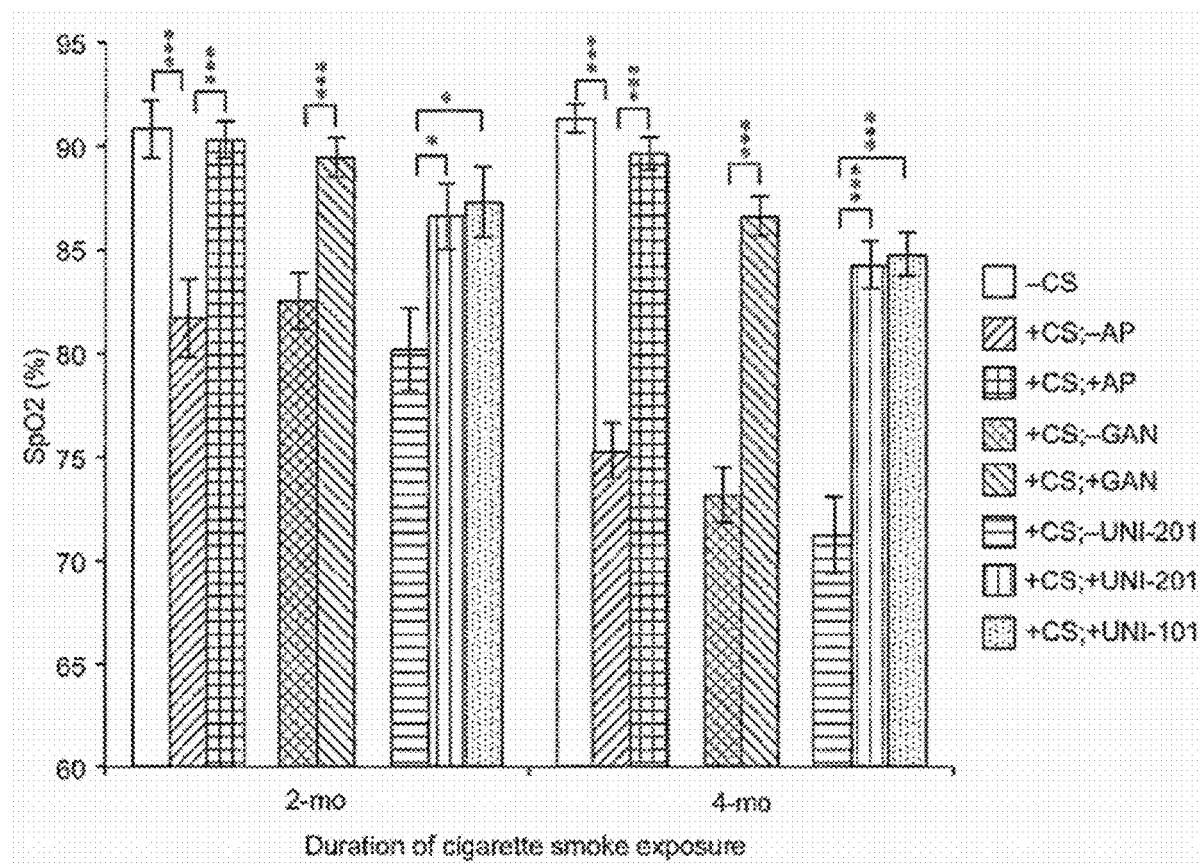

FIG. 5 shows that removing senescent cells helps restore oxygen saturation ($SPO_2$) in a mouse model for cigarette smoke (CS) induced COPD (chronic obstructive pulmonary disease).

Figure 6:
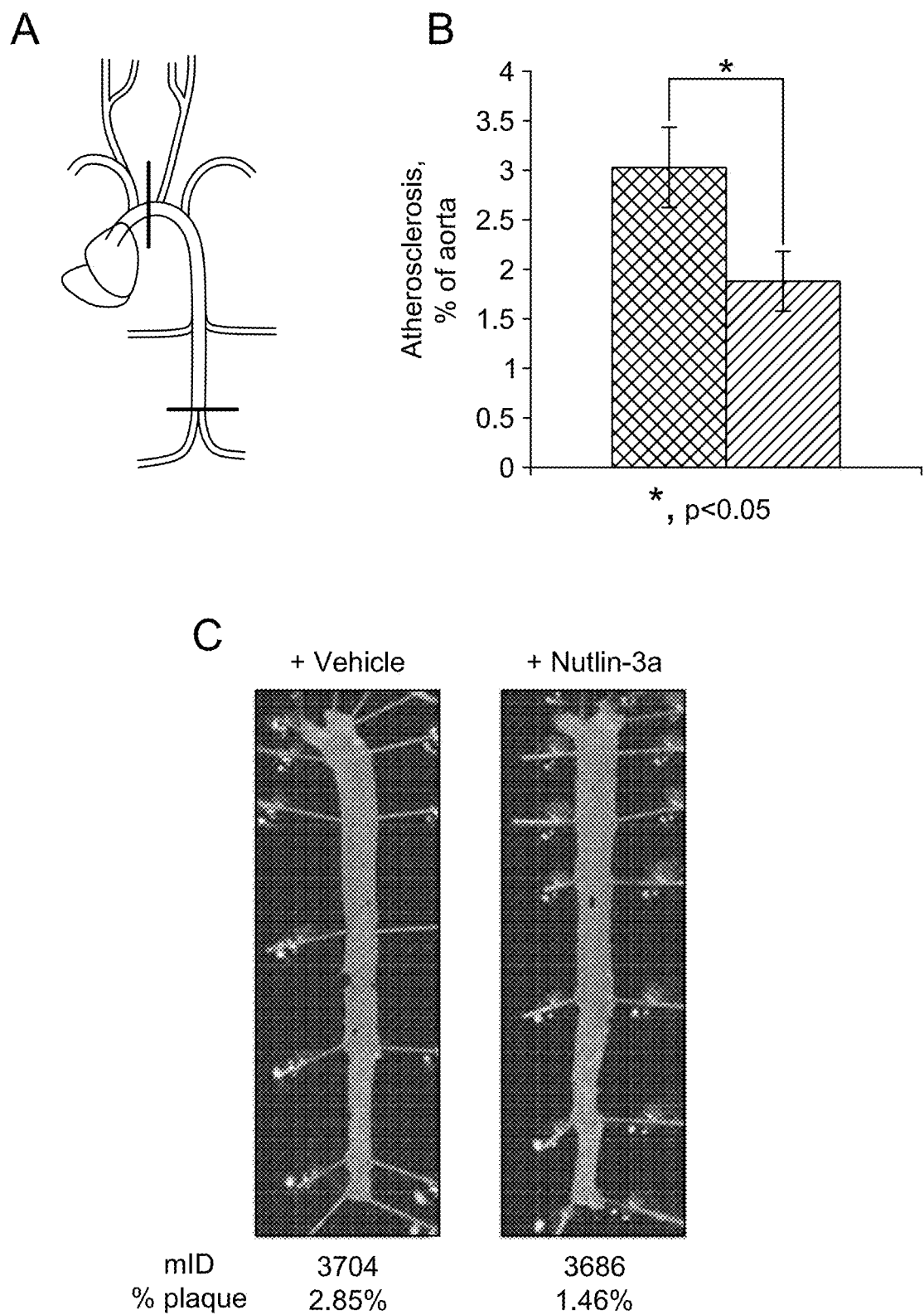

FIG. 6 shows data taken from a mouse model for atherosclerosis, in which inbred mice lacking the LDL receptor were fed a high-fat diet. The right panel shows staining for plaques in the aorta. The middle panel shows quantitatively that the surface area of the aorta covered with plaques was reduced by treatment with a senolytic agent.

DETAILED DESCRIPTION

Senescent cells are characterized as cells that no longer have replicative capacity, but remain in the tissue of origin, eliciting a senescence-associated secretory phenotype (SASP). It is a premise of this disclosure that many age-related conditions are mediated by senescent cells, and that selective removal of the cells from tissues at or around the condition can be used clinically for the treatment of such conditions.

The technology described and claimed below represents the first description of a new class of Bcl inhibitors that can be used to selectively eliminate senescent cells from a target tissue for purposes of treatment of age-related conditions.

Inhibition of Bcl Protein Activity

The Bcl protein family (TC #1.A.21) includes evolutionarily-conserved proteins that share Bcl-2 homology (BH) domains. Bcl proteins are most notable for their ability to up- or down-regulate apoptosis, a form of programmed cell death, at the mitochondrion. The following explanation is provided to assist the user in understanding some of the scientific underpinnings of the compounds of this disclosure. These concepts are not needed to practice the invention, nor do they limit the use of the compounds and methods described here in any manner beyond that which is expressly stated or required.

In the context of this disclosure, the Bcl proteins of particular interest are those that downregulate apoptosis. Anti-apoptotic Bcl proteins contain BH1 and BH2 domains, some of them contain an additional N-terminal BH4 domain (Bcl-2, Bcl-x(L) and Bcl-w (Bcl-2L2), Inhibiting these proteins increases the rate or susceptibility of cells to apoptosis. Thus, an inhibitor of such proteins can be used to help eliminate cells in which the proteins are expressed.

In the mid-2000s, Abbott Laboratories developed a novel inhibitor of Bcl-2, Bcl-xL and Bcl-w, known as ABT-737 (Navitoclax). This compound is part of a group of BH3 mimetic small molecule inhibitors (SMI) that target these Bcl-2 family proteins, but not A1 or Mcl-1. ABT-737 is superior to previous BCL-2 inhibitors given its higher affinity for Bcl-2, Bcl-xL and Bcl-w. In vitro studies showed that primary cells from patients with B-cell malignancies are sensitive to ABT-737. In human patients, ABT-737 is effective against some types of cancer cells, but is subject to dose-limiting thrombocytopenia.

It has now been discovered that the compounds described here fit into the active site of Bcl protein to provide strong Bcl inhibition and/or promote apoptosis of target cells. These compounds can be developed as highly potent and specific drugs to target senescent cells and cancer cells, as described in the sections that follow.

Model Compounds

Many of the compounds of this invention have a structure that falls within the scope of the formula shown below.

wherein:
$X_1$ is halide, preferably —Cl;
$X_2$ is —COOH;
$X_3$ is —SO$_2$CF$_3$; —SO$_2$CH$_3$; or —NO$_2$
$X_5$ is —F or —H;
$R_1$ is —CH(CH$_3$)$_2$;
$R_2$ is either —H or —CH$_3$, preferably —CH$_3$;
$R_3$ and $R_4$ are independently either —H or —CH$_3$, preferably both —H;
$n_1$ is 1 to 3, preferably 2; and
$R_6$ is selected from —OH, —N⌬—OH, and —N⌬—CH$_2$OH;

wherein the hydroxyl group in $R_6$ is optionally phosphorylated.

Any of the possible constituents in the formula come with the proviso that if $X_3$ is —SO$_2$CF$_3$, then the hydroxyl group in $R_6$ must be phosphorylated. In combination with any of the aforelisted options, the —COOH group of $X_2$ may be phosphorylated as well as or instead of the hydroxyl group, at the user's option.

A "phosphorylated" form of a compound is a compound in which one or more —OH or —COOH groups have been substituted with a phosphate group which is either —OPO$_3$H$_2$ or —C$_n$PO$_3$H$_2$ (where n is 1 to 4), such that the phosphate group may be removed in vivo (for example, by enzymolysis). A non-phosphorylated or dephosphorylated form has no such group.

Unless explicitly stated or otherwise required, compounds depicted without stereochemistry include a racemic mixture of all stereoisomers, and enantiomerically pure preparations with either enantiomer as an alternative. Any of the compounds of Formula I typically but don't necessarily have the stereochemistry depicted in Formula I below:

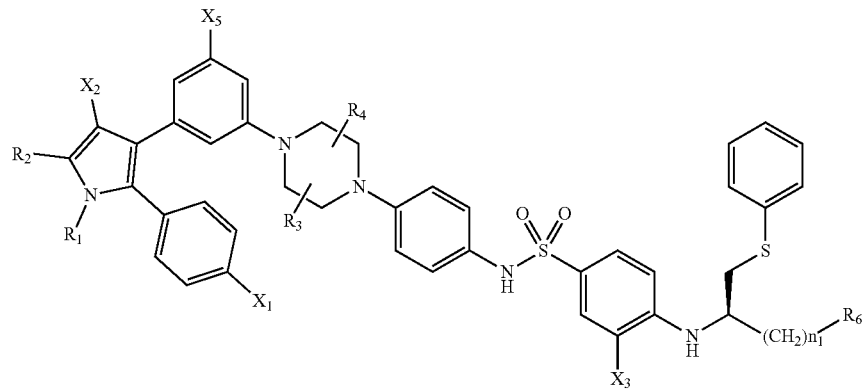

which can also be depicted as follows:

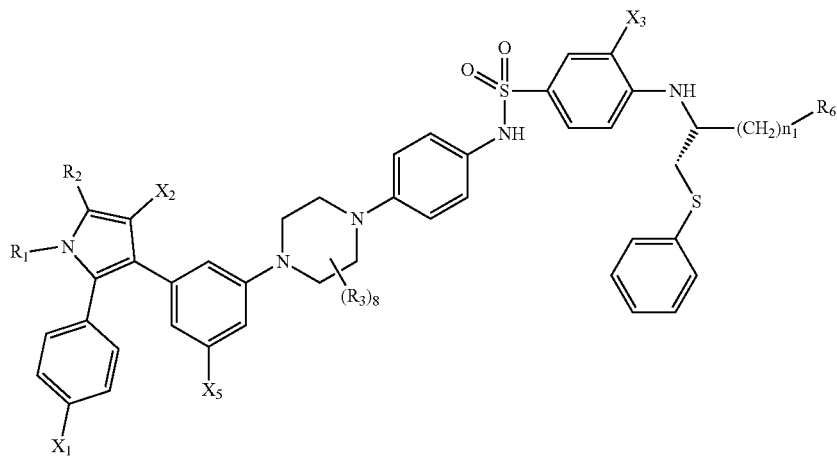

wherein each R$_3$ is independently either —H or —CH$_3$.

Many of the compounds of this invention have a structure that falls within the scope of Formula II shown below.

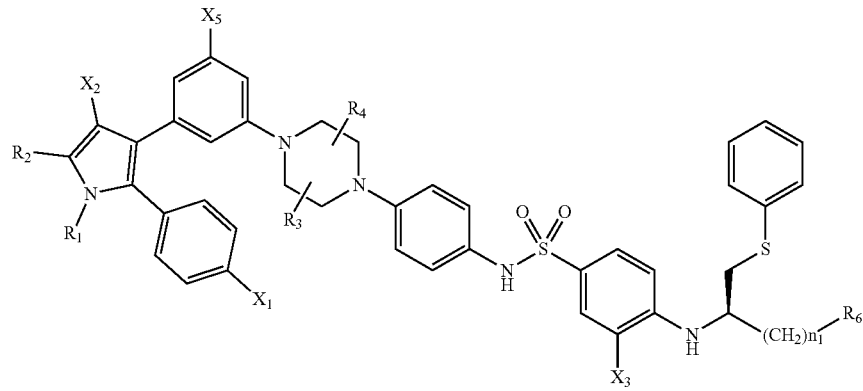

which can also be depicted as follows:

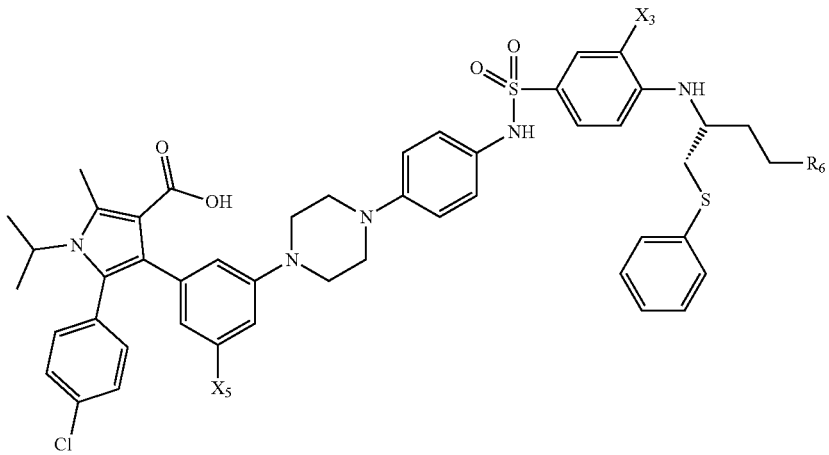

wherein:
X₁ is —Cl;
X₂ is —COOH;
X₃ is —SO₂CF₃; —SO₂CH₃; or —NO₂
X₅ is —F or —H;
R₁ is —CH(CH₃)₂;
R₂ is —CH₃;
R₃ and R₄ are both —H;
n₁ is 2; and
R₆ is selected from —OR₇,

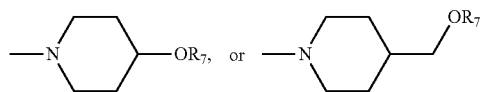

and
R₇ is —H, —P(O)(OH)₂, or —(C$_n$H$_{2n}$)P(O)(OH)₂ (where n is 1 to 4 or 1 to 8);

with the proviso that if X₃ is —SO₂CF₃, then R₇ is —P(O)(OH)₂ or —(C$_n$H$_{2n}$)P(O)(OH)₂.

This includes separately and together both the acid forms of R₇ as shown, and salt forms thereof, such as when R₇ is —P(O)(ONa)₂ or —(C$_n$H$_{2n}$)P(O)(ONa)₂.

As compositions of matter or for use in particular contexts, each chemical species listed in this disclosure and/or each structural formula may optionally be put into use or claimed with the proviso that it is not explicitly and exactly depicted or described in any of U.S. Pat. Nos. 8,691,184, 9,096,625, and 9,403,856 (Wang et al.). Each chemical species listed in this disclosure and/or each structural formula may optionally be put into use or claimed with the proviso that it is not explicitly and exactly depicted or described in US 20170266211 A1 (David et al.).

Exemplary compounds that may qualify for preparation and/or use in accordance with this disclosure are shown in TABLE 1A.

TABLE 1A

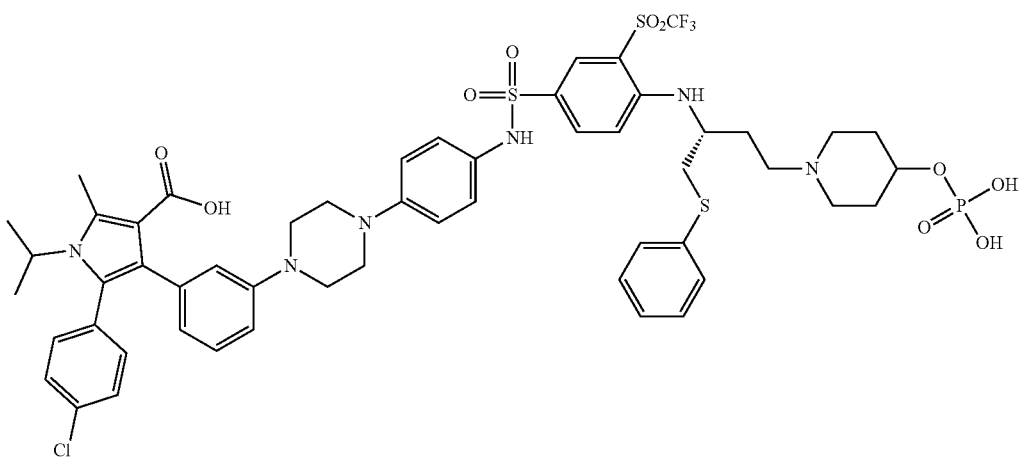

(R)-5-(4-chlorophenyl)-1-isopropyl-2-methyl-4-(3-(4-(4-((4-((1-(phenylthio)-4-(4-(phosphonooxy)piperidin-1-yl)butan-2-yl)amino)-3-((trifluoromethyl)sulfonyl)phenyl)sulfonamido)phenyl)piperazin-1-yl)phenyl)-1H-pyrrole-3-carboxylic acid TABLE 1A-continued

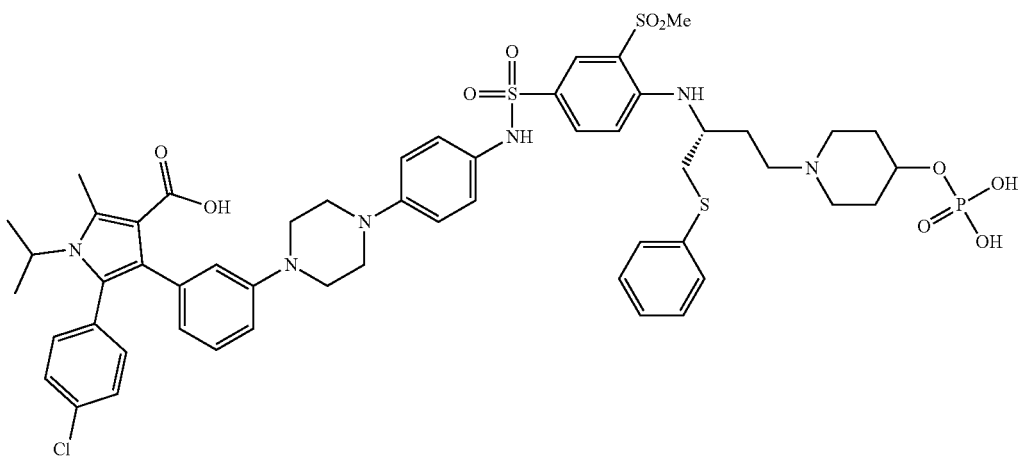 [SMILES: Cc1c(C(=O)O)c(-c2cccc(N3CCN(c4ccc(NS(=O)(=O)c5ccc(N[C@H](CCN6CCC(OP(=O)(O)O)CC6)CSc6ccccc6)c(S(C)(=O)=O)c5)cc4)CC3)c2)c(-c2ccc(Cl)cc2)n1C(C)C]

(R)-5-(4-chlorophenyl)-1-isopropyl-2-methyl-4-(3-(4-(4-(((3-(methylsulfonyl)-4-((1-(phenylthio)-4-(4-(phosphonooxy)piperidin-1-yl)butan-2-yl)amino)phenyl)sulfonamido)phenyl)piperazin-1-yl)phenyl)-1H-pyrrole-3-carboxylic acid

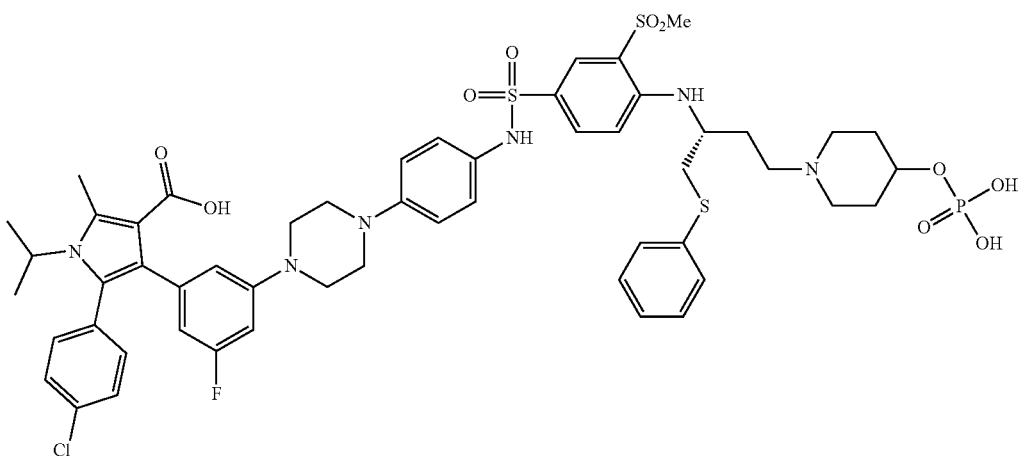 [SMILES: Cc1c(C(=O)O)c(-c2cc(F)cc(N3CCN(c4ccc(NS(=O)(=O)c5ccc(N[C@H](CCN6CCC(OP(=O)(O)O)CC6)CSc6ccccc6)c(S(C)(=O)=O)c5)cc4)CC3)c2)c(-c2ccc(Cl)cc2)n1C(C)C]

(R)-5-(4-chlorophenyl)-4-(3-fluoro-5-(4-(4-(((3-(methylsulfonyl)-4-((1-(phenylthio)-4-(4-(phosphonooxy)piperidin-1-yl)butan-2-yl)amino)phenyl)sulfonamido)phenyl)piperazin-1-yl)phenyl)-1-isopropyl-2-methyl-1H-pyrrole-3-carboxylic acid

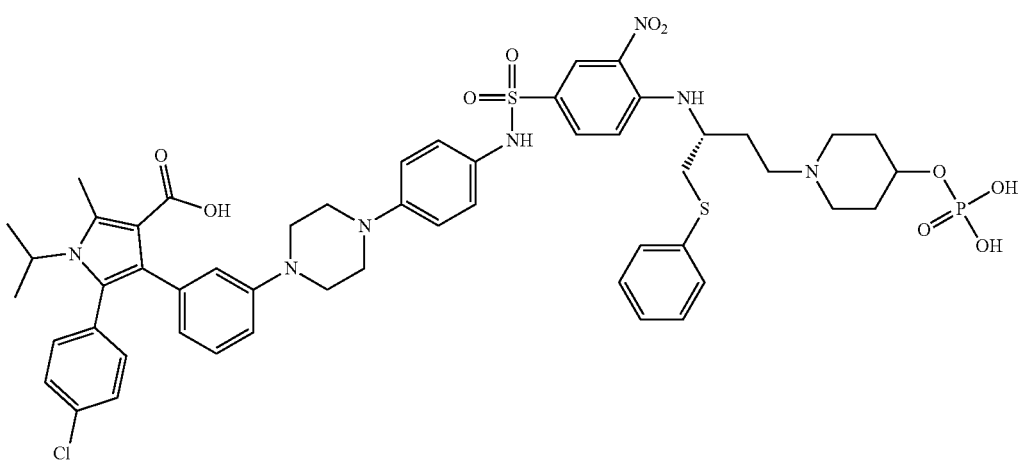

(R)-5-(4-chlorophenyl)-1-isopropyl-2-methyl-4-(3-(4-(4-(((3-nitro-4-((1-(phenylthio)-4-(4-(phosphonooxy)piperidin-1-yl)butan-2-yl)amino)phenyl)sulfonamido)phenyl)piperazin-1-yl)phenyl)-1H-pyrrole-3-carboxylic acid TABLE 1A-continued

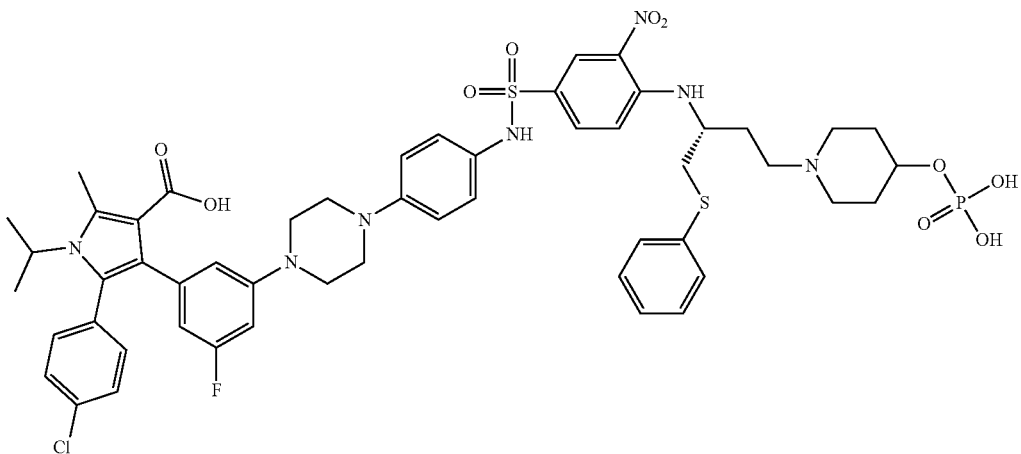 [SMILES: Cc1c(C(=O)O)c(-c2cc(F)cc(N3CCN(c4ccc(NS(=O)(=O)c5ccc(N[C@H](CCN6CCC(OP(=O)(O)O)CC6)CSc6ccccc6)c([N+](=O)[O-])c5)cc4)CC3)c2)c(-c2ccc(Cl)cc2)n1C(C)C]

(R)-5-(4-chlorophenyl)-4-(3-fluoro-5-(4-(4-((3-nitro-4-((1-(phenylthio)-4-(4-(phosphonooxy)piperidin-1-yl)butan-2-yl)amino)phenyl)sulfonamido)phenyl)piperazin-1-yl)phenyl)-1-isopropyl-2-methyl-1H-pyrrole-3-carboxylic acid

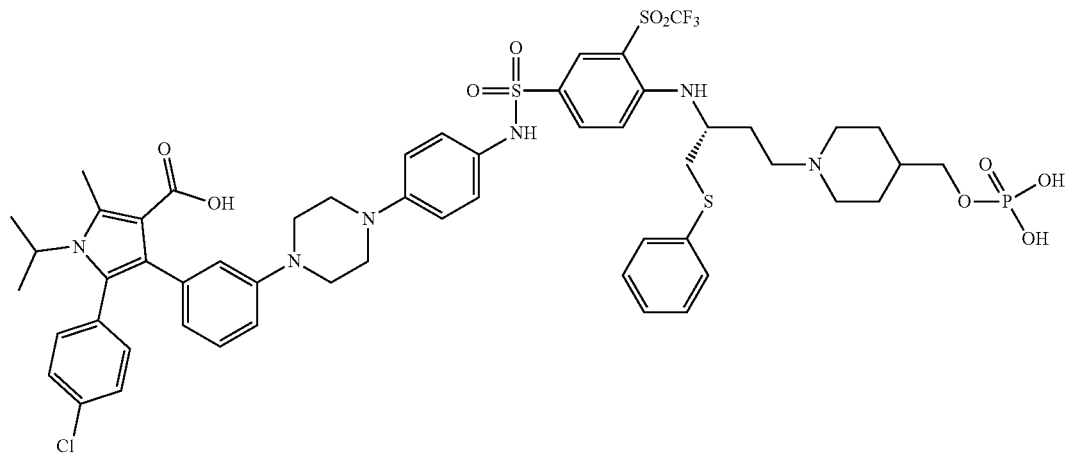

(R)-5-(4-chlorophenyl)-1-isopropyl-2-methyl-4-(3-(4-(4-((4-(((1-(phenylthio)-4-(4-((phosphonooxy)methyl)piperidin-1-yl)butan-2-yl)amino)-3-((trifluoromethyl)sulfonyl)phenyl)sulfonamido)phenyl)piperazin-1-yl)phenyl)-1H-pyrrole-3-carboxylic acid

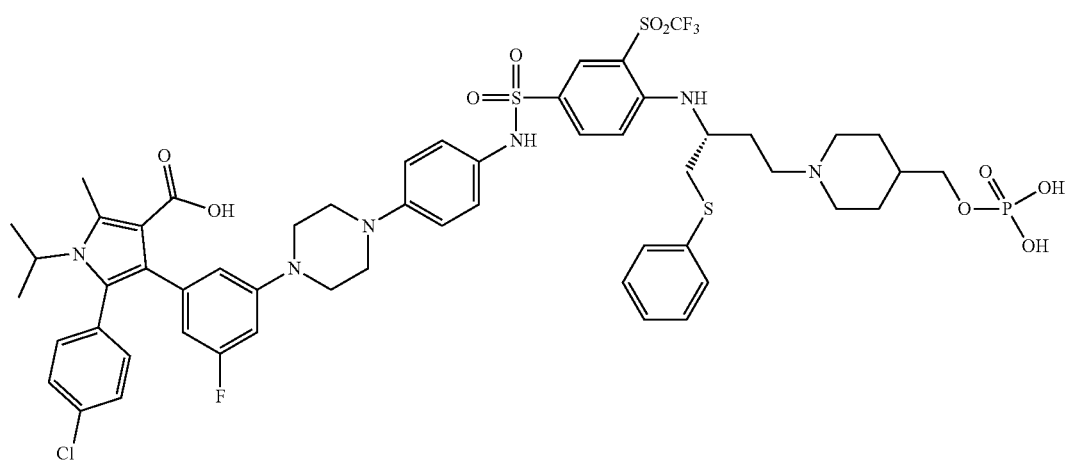

(R)-5-(4-chlorophenyl)-4-(3-fluoro-5-(4-(4-((4-(((1-(phenylthio)-4-(4-((phosphonooxy)methyl)piperidin-1-yl)butan-2-yl)amino)-3-((trifluoromethyl)sulfonyl)phenyl)sulfonamido)phenyl)piperazin-1-yl)phenyl)-1-isopropyl-2-methyl-1H-pyrrole-3-carboxylic acid TABLE 1A-continued

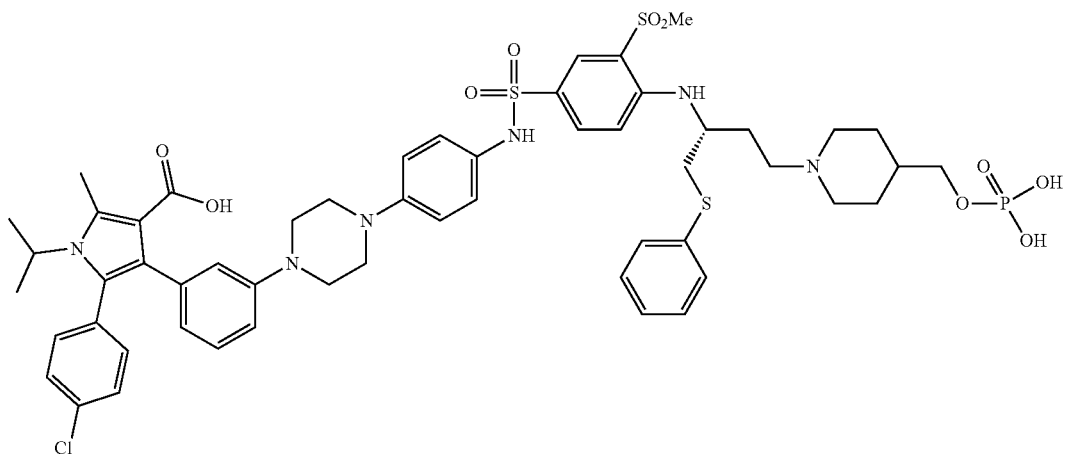

(R)-5-(4-chlorophenyl)-1-isopropyl-2-methyl-4-(3-(4-(4-((3-(methylsulfonyl)-4-((1-(phenylthio)-4-(4-((phosphonooxy)methyl)piperidin-1-yl)butan-2-yl)amino)phenyl)sulfonamido)phenyl)piperazin-1-yl)phenyl)-1H-pyrrole-3-carboxylic acid

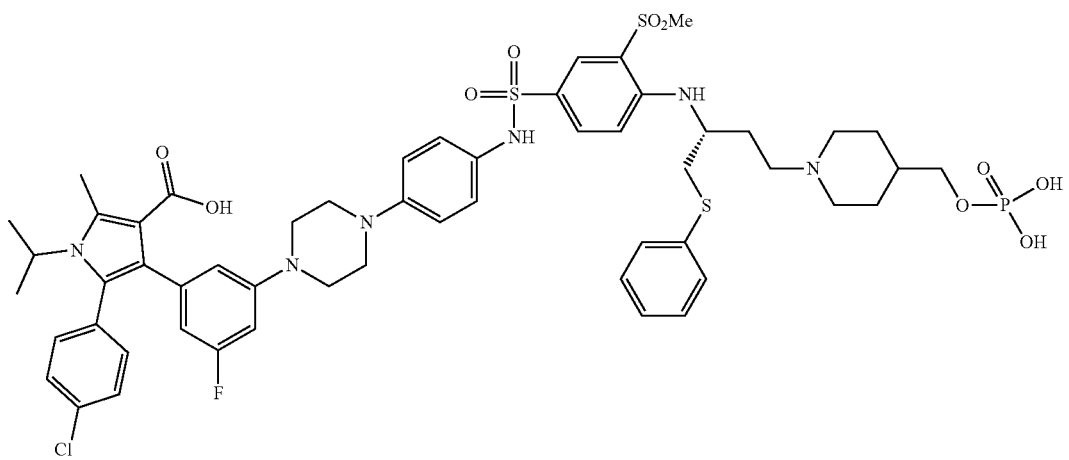 [SMILES: Cc1c(C(=O)O)c(-c2cc(F)cc(N3CCN(c4ccc(NS(=O)(=O)c5ccc(N[C@H](CCN6CCC(COP(=O)(O)O)CC6)CSc6ccccc6)c(S(C)(=O)=O)c5)cc4)CC3)c2)c(-c2ccc(Cl)cc2)n1C(C)C]

(R)-5-(4-chlorophenyl)-4-(3-fluoro-5-(4-(4-((3-(methylsulfonyl)-4-((1-(phenylthio)-4-(4-((phosphonooxy)methyl)piperidin-1-yl)butan-2-yl)amino)phenyl)sulfonamido)phenyl)piperazin-1-yl)phenyl)-1-isopropyl-2-methyl-1H-pyrrole-3-carboxylic acid

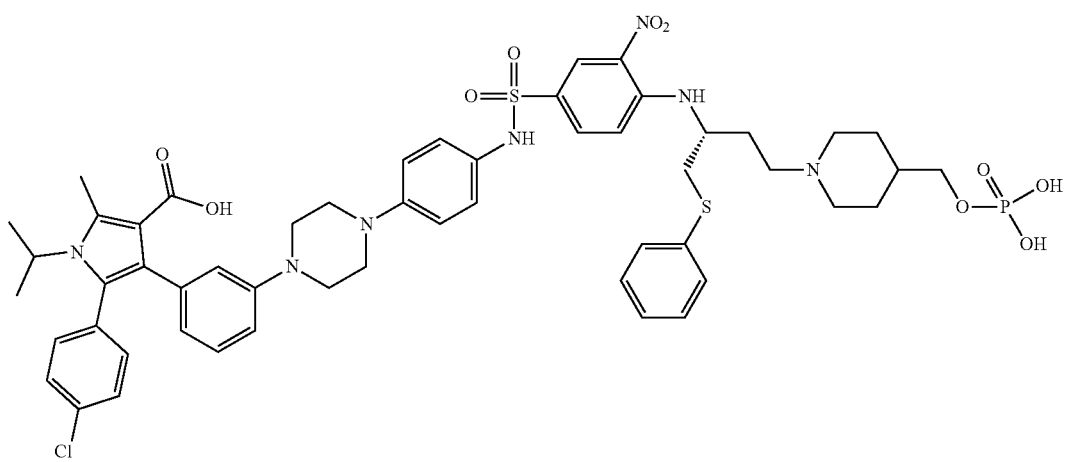 [SMILES: Cc1c(C(=O)O)c(-c2cccc(N3CCN(c4ccc(NS(=O)(=O)c5ccc(N[C@H](CCN6CCC(COP(=O)(O)O)CC6)CSc6ccccc6)c([N+](=O)[O-])c5)cc4)CC3)c2)c(-c2ccc(Cl)cc2)n1C(C)C]

(R)-5-(4-chlorophenyl)-1-isopropyl-2-methyl-4-(3-(4-(4-((3-nitro-4-((1-(phenylthio)-4-(4-((phosphonooxy)methyl)piperidin-1-yl)butan-2-yl)amino)phenyl)sulfonamido)phenyl)piperazin-1-yl)phenyl)-1H-pyrrole-3-carboxylic acid TABLE 1A-continued

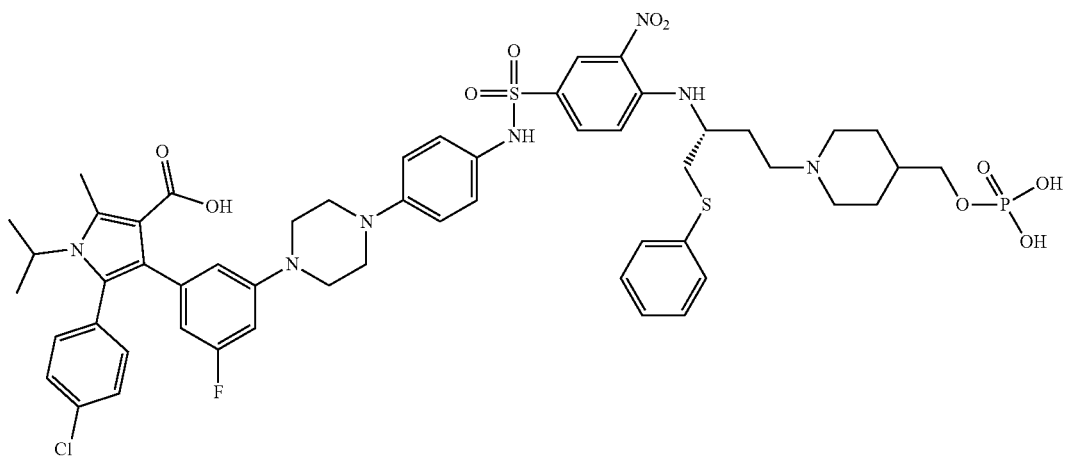 [SMILES: Cc1c(C(=O)O)c(-c2cc(F)cc(N3CCN(c4ccc(NS(=O)(=O)c5ccc(N[C@H](CCN6CCC(COP(=O)(O)O)CC6)CSc6ccccc6)c([N+](=O)[O-])c5)cc4)CC3)c2)c(-c2ccc(Cl)cc2)n1C(C)C]

(R)-5-(4-chlorophenyl)-4-(3-fluoro-5-(4-(4-(4-((3-nitro-4-((1-(phenylthio)-4-(4-((phosphonooxy)methyl)piperidin-1-yl)butan-2-yl)amino)phenyl)sulfonamido)phenyl)piperazin-1-yl)phenyl)-1-isopropyl-2-methyl-1H-pyrrole-3-carboxylic acid

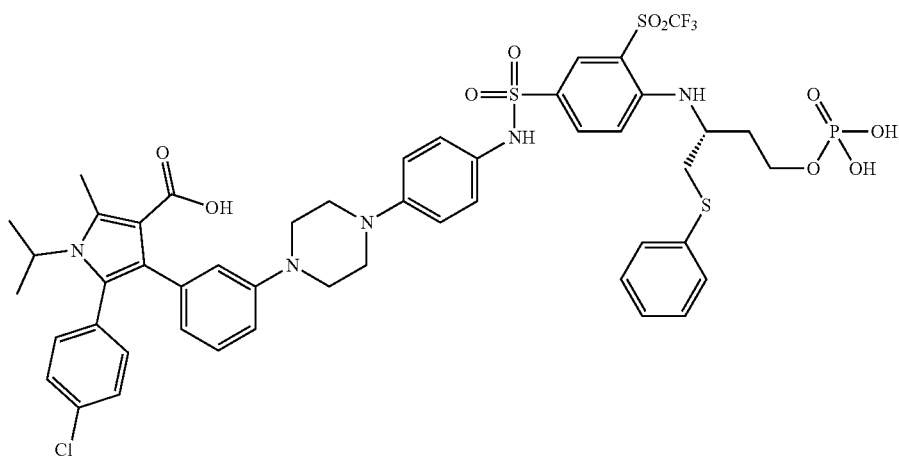

(R)-5-(4-chlorophenyl)-1-isopropyl-2-methyl-4-(3-(4-(4-((4-((1-(phenylthio)-4-(phosphonooxy)butan-2-yl)amino)-3-((trifluoromethyl)sulfonyl)phenyl)sulfonamido)phenyl)piperazin-1-yl)phenyl)-1H-pyrrole-3-carboxylic acid

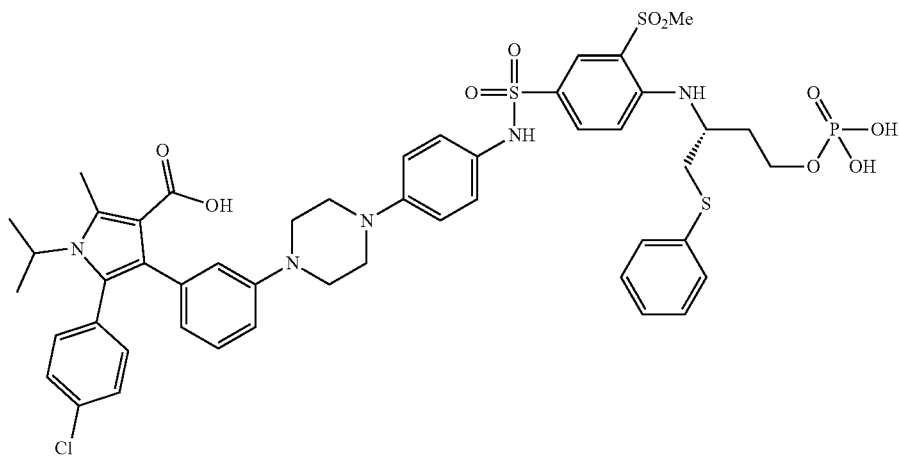 [SMILES: Cc1c(C(=O)O)c(-c2cccc(N3CCN(c4ccc(NS(=O)(=O)c5ccc(N[C@H](CCOP(=O)(O)O)CSc6ccccc6)c(S(C)(=O)=O)c5)cc4)CC3)c2)c(-c2ccc(Cl)cc2)n1C(C)C]

(R)-5-(4-chlorophenyl)-1-isopropyl-2-methyl-4-(3-(4-(4-((3-(methylsulfonyl)-4-((1-(phenylthio)-4-(phosphonooxy)butan-2-yl)amino)phenyl)sulfonamido)phenyl)piperazin-1-yl)phenyl)-1H-pyrrole-3-carboxylic acid TABLE 1A-continued

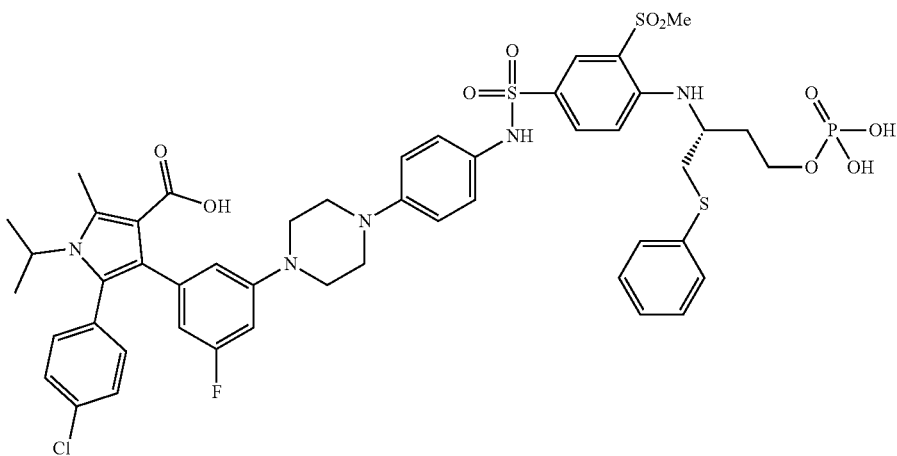 [SMILES: Cc1c(C(=O)O)c(-c2cc(F)cc(N3CCN(c4ccc(NS(=O)(=O)c5ccc(N[C@H](CCOP(=O)(O)O)CSc6ccccc6)c(S(C)(=O)=O)c5)cc4)CC3)c2)c(-c2ccc(Cl)cc2)n1C(C)C]

(R)-5-(4-chlorophenyl)-4-(3-fluoro-5-(4-(4-((3-(methylsulfonyl)-4-((1-(phenylthio)-4-(phosphonooxy)butan-2-yl)amino)phenyl)sulfonamido)phenyl)piperazin-1-yl)phenyl)-1-isopropyl-2-methyl-1H-pyrrole-3-carboxylic acid

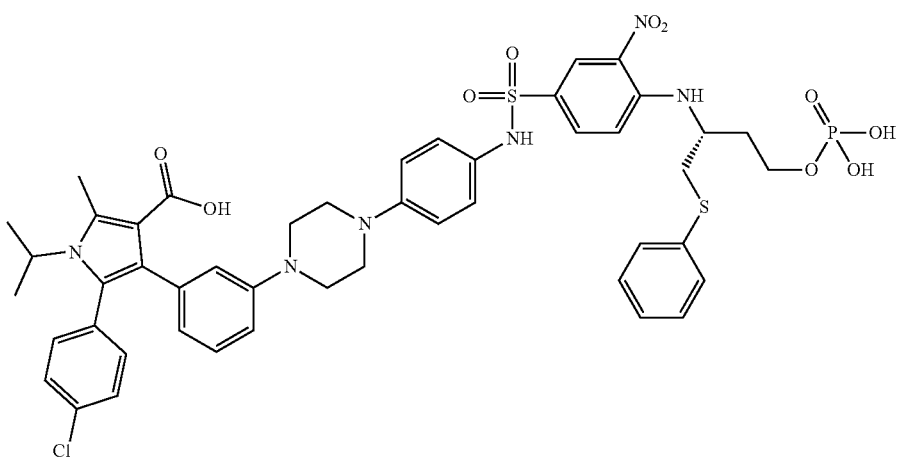

(R)-5-(4-chlorophenyl)-1-isopropyl-2-methyl-4-(3-(4-(4-((3-nitro-4-((1-(phenylthio)-4-(phosphonooxy)butan-2-yl)amino)phenyl)sulfonamido)phenyl)piperazin-1-yl)phenyl)-1H-pyrrole-3-carboxylic acid

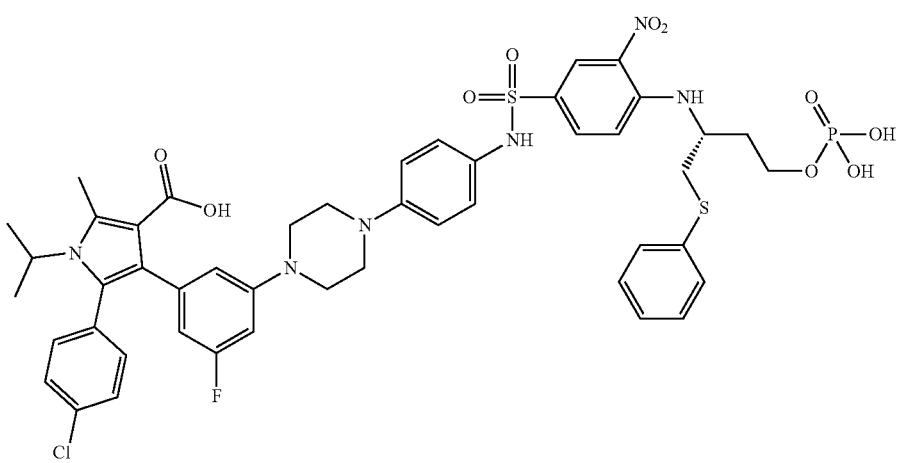 [SMILES: Cc1c(C(=O)O)c(-c2cc(F)cc(N3CCN(c4ccc(NS(=O)(=O)c5ccc(N[C@H](CCOP(=O)(O)O)CSc6ccccc6)c([N+](=O)[O-])c5)cc4)CC3)c2)c(-c2ccc(Cl)cc2)n1C(C)C]

(R)-5-(4-chlorophenyl)-4-(3-fluoro-5-(4-(4-((3-nitro-4-((1-(phenylthio)-4-(phosphonooxy)butan-2-yl)amino)phenyl)sulfonamido)phenyl)piperazin-1-yl)phenyl)-1-isopropyl-2-methyl-1H-pyrrole-3-carboxylic acid TABLE 1A-continued

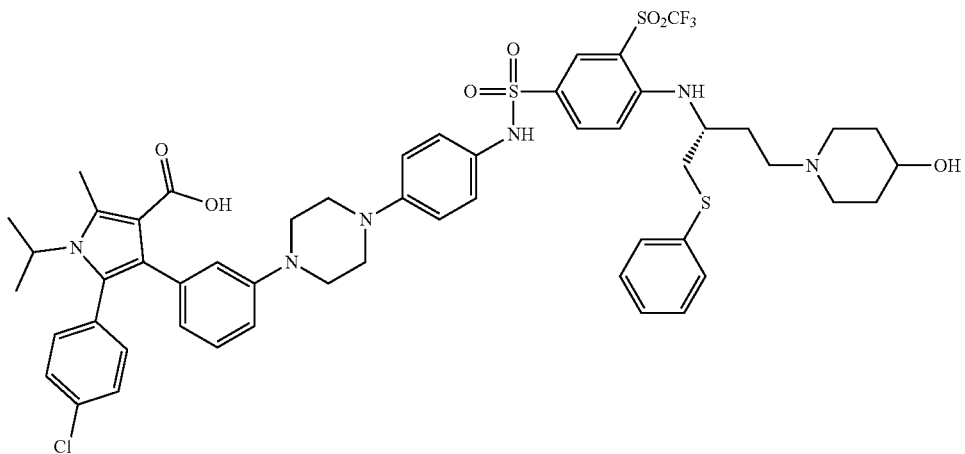

(R)-5-(4-chlorophenyl)-4-(3-(4-(4-((4-((4-(4-hydroxypiperidin-1-yl)-1-(phenylthio)butan-2-yl)amino)-3-((trifluoromethyl)sulfonyl)phenyl)sulfonamido)phenyl)piperazin-1-yl)phenyl)-1-isopropyl-2-methyl-1H-pyrrole-3-carboxylic acid

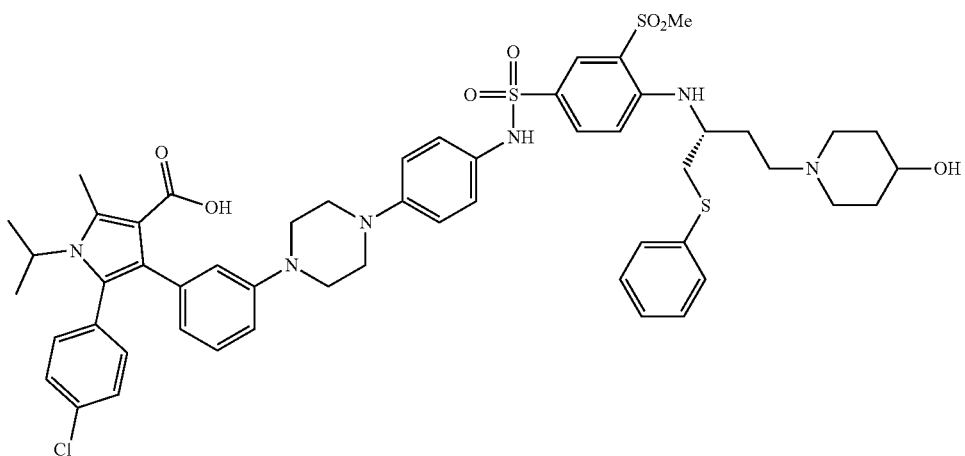 [SMILES: Cc1c(C(=O)O)c(-c2cccc(N3CCN(c4ccc(NS(=O)(=O)c5ccc(N[C@H](CCN6CCC(O)CC6)CSc6ccccc6)c(S(C)(=O)=O)c5)cc4)CC3)c2)c(-c2ccc(Cl)cc2)n1C(C)C]

(R)-5-(4-chlorophenyl)-4-(3-(4-(4-((4-((4-(4-hydroxypiperidin-1-yl)-1-(phenylthio)butan-2-yl)amino)-3-(methylsulfonyl)phenyl)sulfonamido)phenyl)piperazin-1-yl)phenyl)-1-isopropyl-2-methyl-1H-pyrrole-3-carboxylic acid

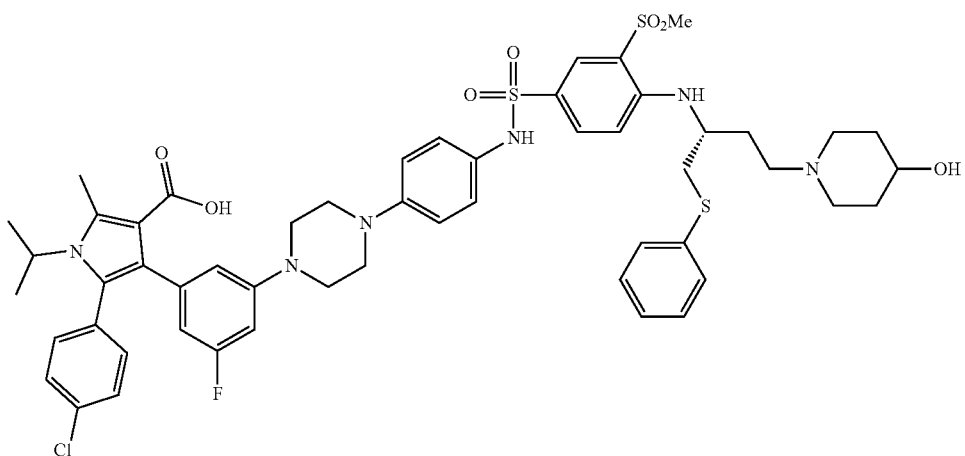

(R)-5-(4-chlorophenyl)-4-(3-fluoro-5-(4-(4-((4-((4-(4-hydroxypiperidin-1-yl)-1-(phenylthio)butan-2-yl)amino)-3-(methylsulfonyl)phenyl)sulfonamido)phenyl)piperazin-1-yl)phenyl)-1-isopropyl-2-methyl-1H-pyrrole-3-carboxylic acid TABLE 1A-continued

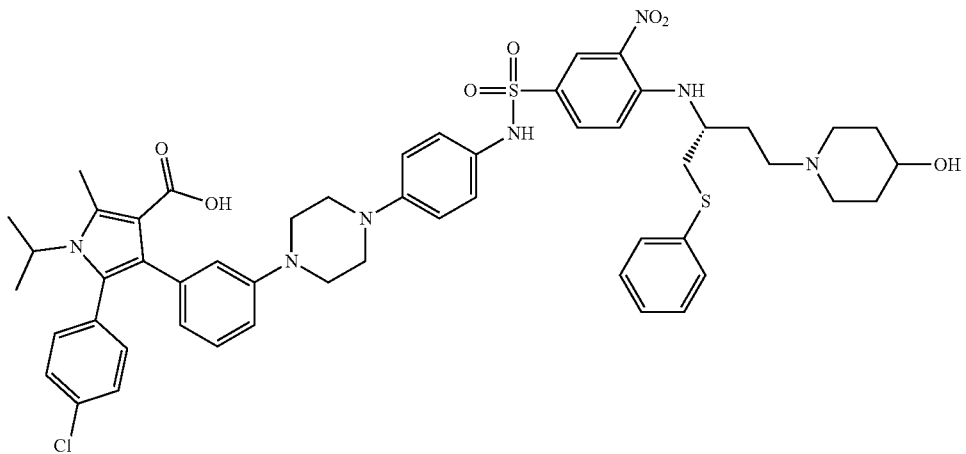 [SMILES: Cc1c(C(=O)O)c(-c2cccc(N3CCN(c4ccc(NS(=O)(=O)c5ccc(N[C@H](CCN6CCC(O)CC6)CSc6ccccc6)c([N+](=O)[O-])c5)cc4)CC3)c2)c(-c2ccc(Cl)cc2)n1C(C)C]

(R)-5-(4-chlorophenyl)-4-(3-(4-(4-((4-((4-(4-hydroxypiperidin-1-yl)-1-(phenylthio)butan-2-yl)amino)-3-nitrophenyl)sulfonamido)phenyl)piperazin-1-yl)phenyl)-1-isopropyl-2-methyl-1H-pyrrole-3-carboxylic acid

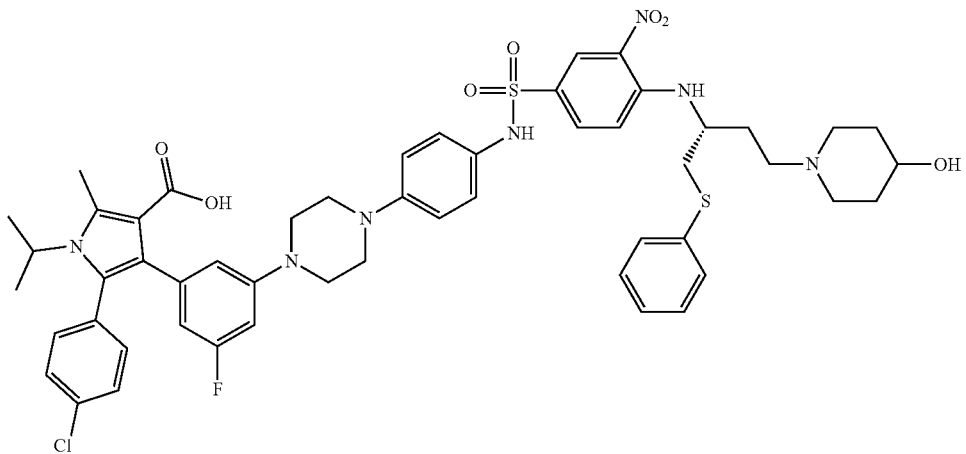 [SMILES: Cc1c(C(=O)O)c(-c2cc(F)cc(N3CCN(c4ccc(NS(=O)(=O)c5ccc(N[C@H](CCN6CCC(O)CC6)CSc6ccccc6)c([N+](=O)[O-])c5)cc4)CC3)c2)c(-c2ccc(Cl)cc2)n1C(C)C]

(R)-5-(4-chlorophenyl)-4-(3-fluoro-5-(4-(4-((4-((4-(4-hydroxypiperidin-1-yl)-1-(phenylthio)butan-2-yl)amino)-3-nitrophenyl)sulfonamido)phenyl)piperazin-1-yl)phenyl)-1-isopropyl-2-methyl-1H-pyrrole-3-carboxylic acid

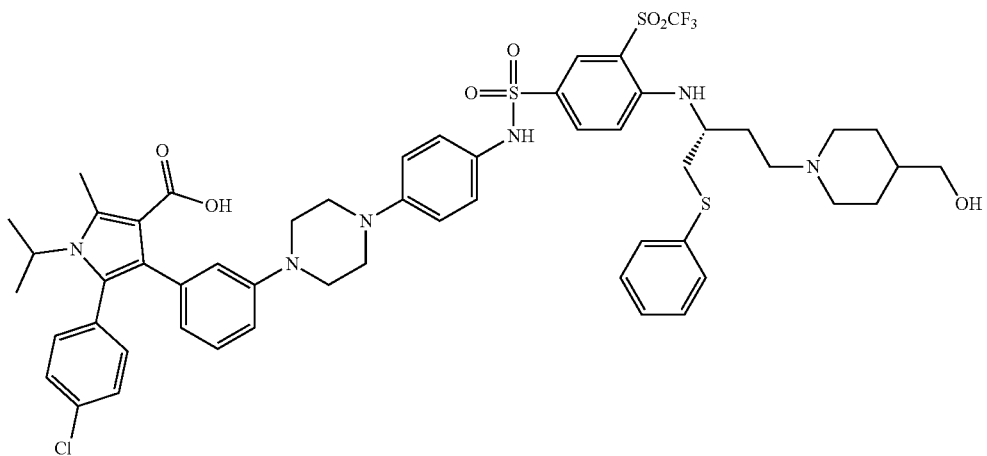

(R)-S-(4-chlorophenyl)-4-(3-(4-(4-((4-((4-(4-(hydroxymethyl)piperidin-1-yl)-1-(phenylthio)butan-2-yl)amino)-3-((trifluoromethyl)sulfonyl)phenyl)sulfonamido)phenyl)piperazin-1-yl)phenyl)-1-isopropyl-2-methyl-1H-pyrrole-3-carboxylic acid TABLE 1A-continued

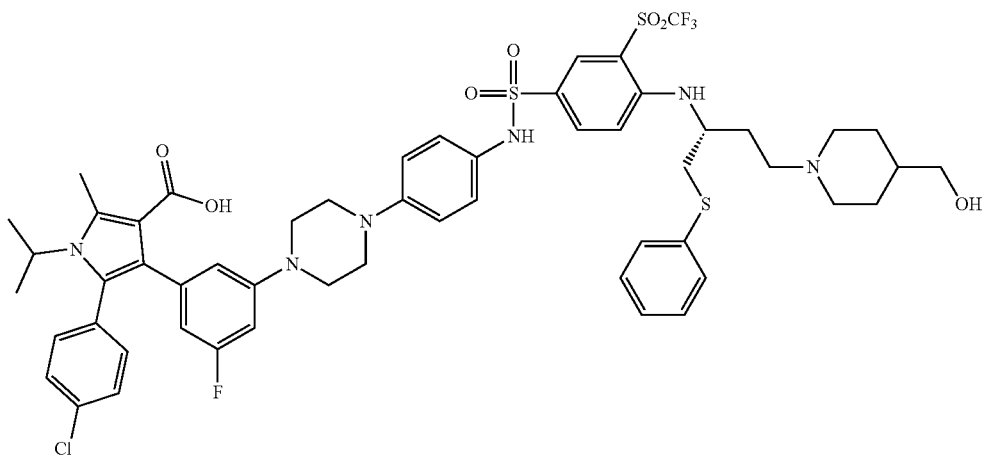

(R)-5-(4-chlorophenyl)-4-(3-fluoro-5-(4-(4-((4-((4-(4-(hydroxymethyl)piperidin-1-yl)-1-(phenylthio)butan-2-yl)amino)-3-((trifluoromethyl)sulfonyl)phenyl)sulfonamido)phenyl)piperazin-1-yl)phenyl)-1-isopropyl-2-methyl-1H-pyrrole-3-carboxylic acid

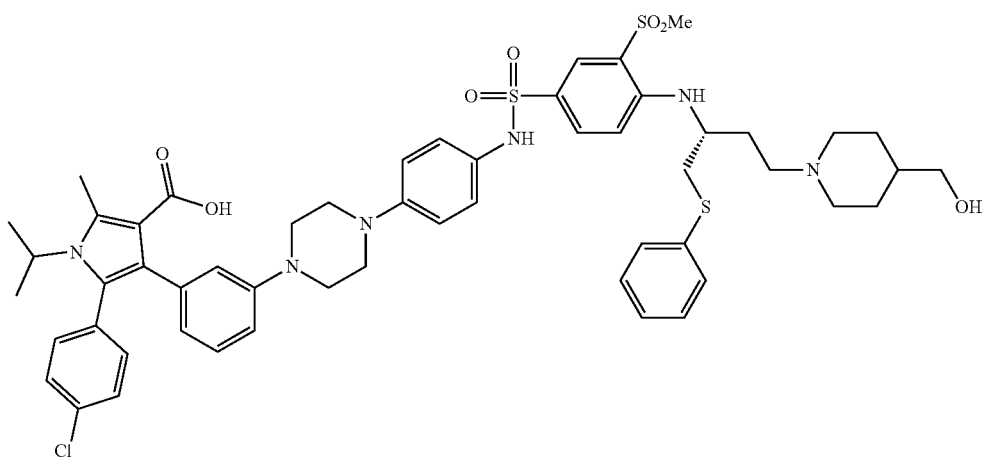 [SMILES: Cc1c(C(=O)O)c(-c2cccc(N3CCN(c4ccc(NS(=O)(=O)c5ccc(N[C@H](CCN6CCC(CO)CC6)CSc6ccccc6)c(S(C)(=O)=O)c5)cc4)CC3)c2)c(-c2ccc(Cl)cc2)n1C(C)C]

(R)-5-(4-chlorophenyl)-4-(3-(4-(4-((4-((4-(4-(hydroxymethyl)piperidin-1-yl)-1-(phenylthio)butan-2-yl)amino)-3-(methylsulfonyl)phenyl)sulfonamido)phenyl)piperazin-1-yl)phenyl)-1-isopropyl-2-methyl-1H-pyrrole-3-carboxylic acid

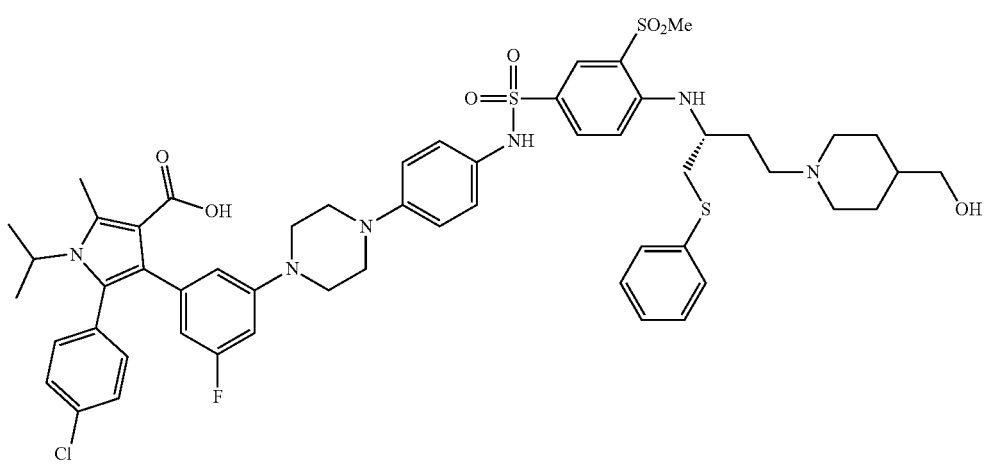 [SMILES: Cc1c(C(=O)O)c(-c2cc(F)cc(N3CCN(c4ccc(NS(=O)(=O)c5ccc(N[C@H](CCN6CCC(CO)CC6)CSc6ccccc6)c(S(C)(=O)=O)c5)cc4)CC3)c2)c(-c2ccc(Cl)cc2)n1C(C)C]

(R)-5-(4-chlorophenyl)-4-(3-fluoro-5-(4-(4-((4-((4-(4-(hydroxymethyl)piperidin-1-yl)-1-(phenylthio)butan-2-yl)amino)-3-(methylsulfonyl)phenyl)sulfonamido)phenyl)piperazin-1-yl)phenyl)-1-isopropyl-2-methyl-1H-pyrrole-3-carboxylic acid

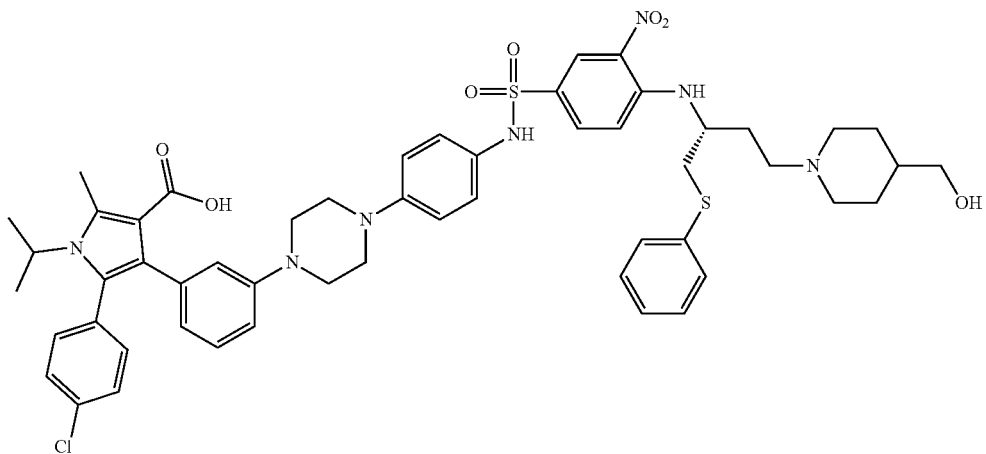 [SMILES: Cc1c(C(=O)O)c(-c2cccc(N3CCN(c4ccc(NS(=O)(=O)c5ccc(N[C@H](CCN6CCC(CO)CC6)CSc6ccccc6)c([N+](=O)[O-])c5)cc4)CC3)c2)c(-c2ccc(Cl)cc2)n1C(C)C]

(R)-5-(4-chlorophenyl)-4-(3-(4-(4-((4-((4-(4-(hydroxymethyl)piperidin-1-yl)-1-(phenylthio)butan-2-yl)amino)-3-nitrophenyl)sulfonamido)phenyl)piperazin-1-yl)phenyl)-1-isopropyl-2-methyl-1H-pyrrole-3-carboxylic acid

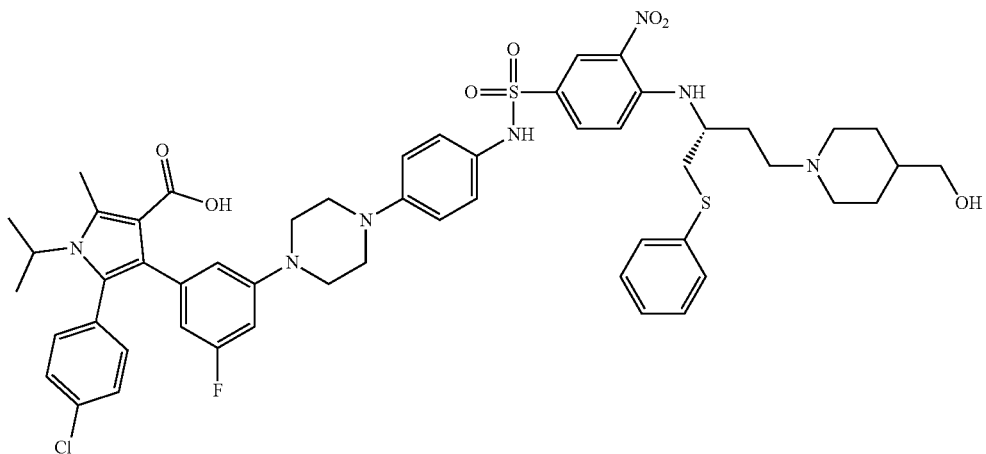 [SMILES: Cc1c(C(=O)O)c(-c2cc(F)cc(N3CCN(c4ccc(NS(=O)(=O)c5ccc(N[C@H](CCN6CCC(CO)CC6)CSc6ccccc6)c([N+](=O)[O-])c5)cc4)CC3)c2)c(-c2ccc(Cl)cc2)n1C(C)C]

(R)-5-(4-chlorophenyl)-4-(3-fluoro-5-(4-(4-((4-((4-(4-(hydroxymethyl)piperidin-1-yl)-1-(phenylthio)butan-2-yl)amino)-3-nitrophenyl)sulfonamido)phenyl)piperazin-1-yl)phenyl)-1-isopropyl-2-methyl-1H-pyrrole-3-carboxylic acid

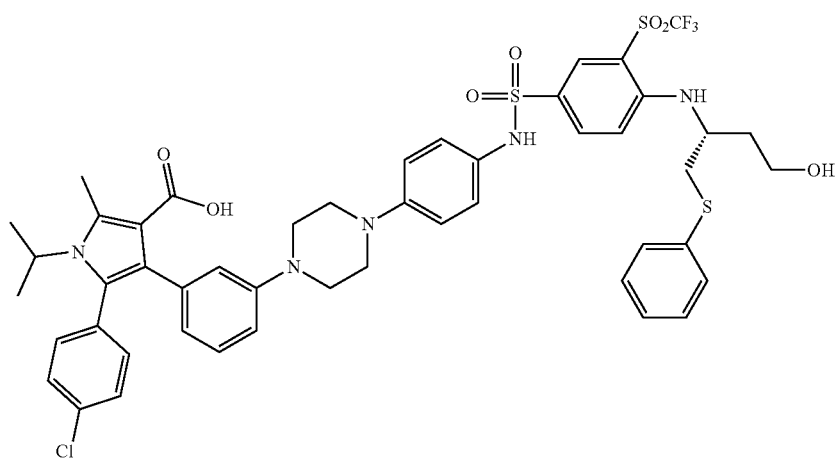

(R)-5-(4-chlorophenyl)-4-(3-(4-(4-((4-((4-hydroxy-1-(phenylthio)butan-2-yl)amino)-3-((trifluoromethyl)sulfonyl)phenyl)sulfonamido)phenyl)piperazin-1-yl)phenyl)-1-isopropyl-2-methyl-1H-pyrrole-3-carboxylic acid TABLE 1A-continued

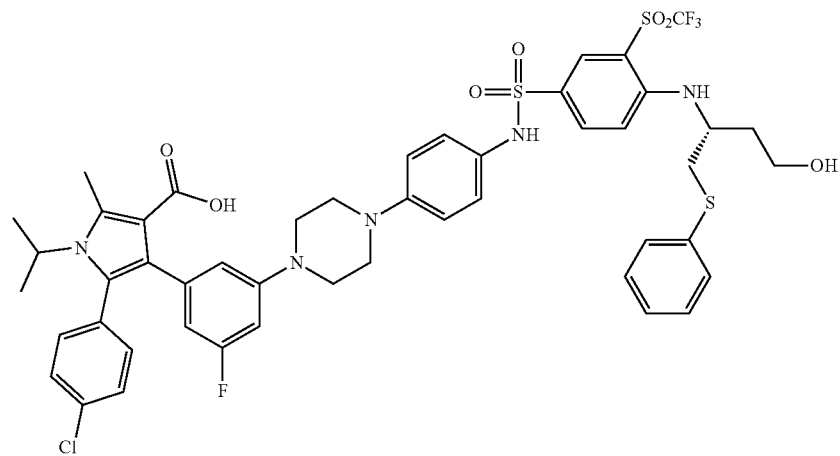

(R)-5-(4-chlorophenyl)-4-(3-fluoro-5-(4-(4-((4-((4-hydroxy-1-(phenylthio)butan-2-yl)amino)-3-((trifluoromethyl)sulfonyl)phenyl)sulfonamido)phenyl)piperazin-1-yl)phenyl)-1-isopropyl-2-methyl-1H-pyrrole-3-carboxylic acid

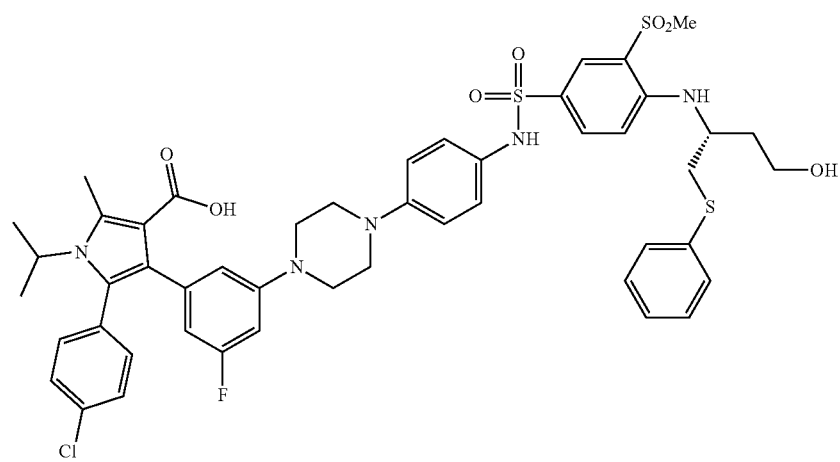 [SMILES: Cc1c(C(=O)O)c(-c2cc(F)cc(N3CCN(c4ccc(NS(=O)(=O)c5ccc(N[C@H](CCO)CSc6ccccc6)c(S(C)(=O)=O)c5)cc4)CC3)c2)c(-c2ccc(Cl)cc2)n1C(C)C]

(R)-5-(4-chlorophenyl)-4-(3-fluoro-5-(4-(4-((4-((4-hydroxy-1-(phenylthio)butan-2-yl)-amino)-3-(methylsulfonyl)phenyl)sulfonamido)phenyl)piperazin-1-yl)phenyl)-1-isopropyl-2-methyl-1H-pyrrole-3-carboxylic acid

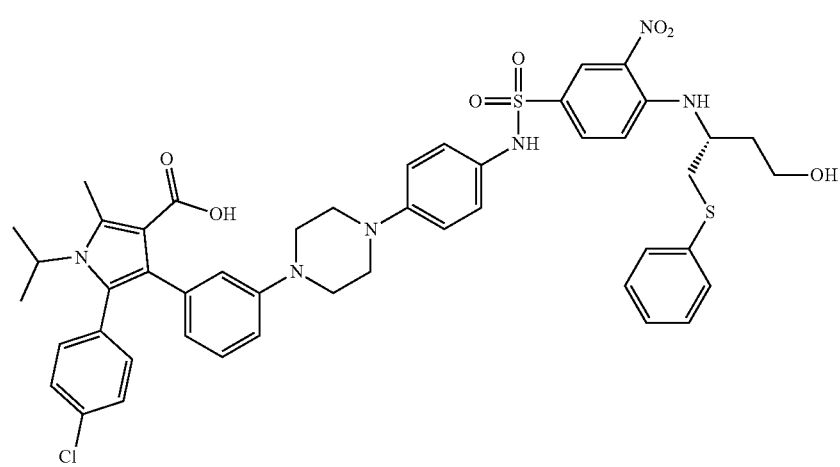 [SMILES: Cc1c(C(=O)O)c(-c2cccc(N3CCN(c4ccc(NS(=O)(=O)c5ccc(N[C@H](CCO)CSc6ccccc6)c([N+](=O)[O-])c5)cc4)CC3)c2)c(-c2ccc(Cl)cc2)n1C(C)C]

(R)-5-(4-chlorophenyl)-4-(3-(4-(4-((4-((4-hydroxy-1-(phenylthio)butan-2-yl)amino)-3-nitrophenyl)sulfonamido)phenyl)piperazin-1-yl)phenyl)-1-isopropyl-2-methyl-1H-pyrrole-3-carboxylic acid TABLE 1A-continued

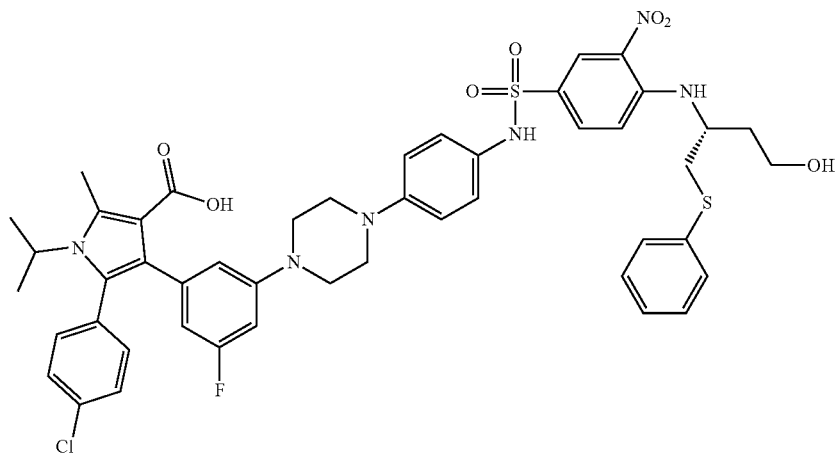 [SMILES: Cc1c(C(=O)O)c(-c2cc(F)cc(N3CCN(c4ccc(NS(=O)(=O)c5ccc(N[C@H](CCO)CSc6ccccc6)c([N+](=O)[O-])c5)cc4)CC3)c2)c(-c2ccc(Cl)cc2)n1C(C)C]

(R)-5-(4-chlorophenyl)-4-(3-fluoro-5-(4-(4-((4-((4-hydroxy-1-(phenylthio)butan-2-yl)amino)-3-nitrophenyl)sulfonamido)phenyl)piperazin-1-yl)phenyl)-1-isopropyl-2-methyl-1H-pyrrole-3-carboxylic acid

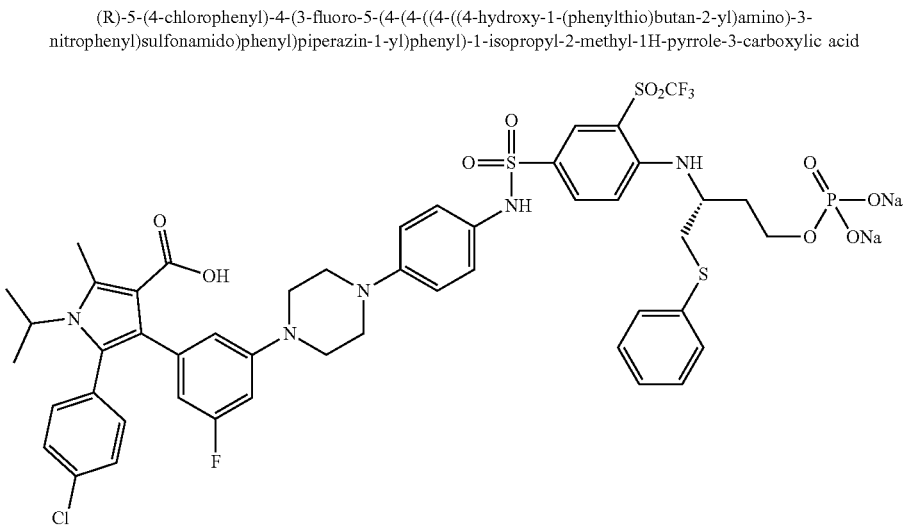

sodium (R)-3-((4-(N-(4-(4-(3-(4-carboxy-2-(4-chlorophenyl)-1-isopropyl-5-methyl-1H-pyrrol-3-yl)-5-fluorophenyl)piperazin-1-yl)phenyl)sulfamoyl)-2-((trifluoromethyl)sulfonyl)phenyl)amino)-4-(phenylthio)butyl phosphate

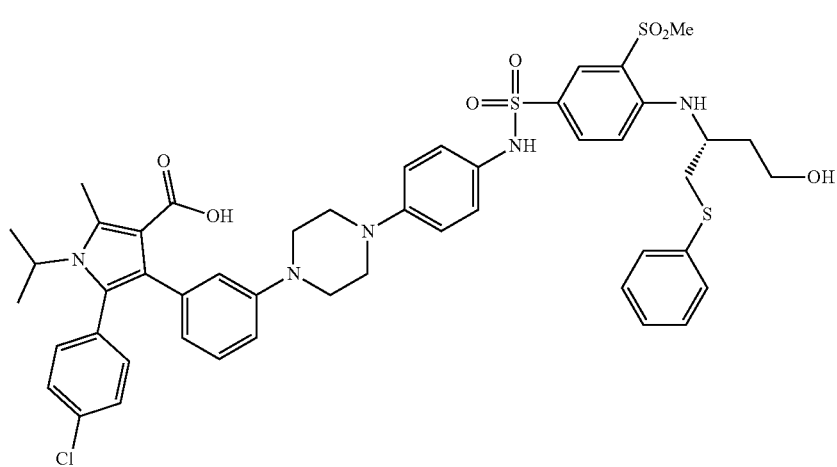

(R)-5-(4-chlorophenyl)-4-(3-(4-(4-((4-((4-hydroxy-1-(phenylthio)bulan-2-yl)amino)-3-(methylsulfonyl)phenyl)sulfonamido)phenyl)piperazin-1-yl)phenyl)-1-isopropyl-2-methyl-1H-pyrrole-3-carboxylic acid Other compounds that can be tested and developed as senolytic agents or for the treatment of senescence associated diseases in accordance with this disclosure include the compounds shown in TABLE 1B:

Alternatively or in addition, compounds can be evaluated for an ability to kill senescent cells specifically. Cultured cells are contacted with the compound, and the degree of cytotoxicity or inhibition of the cells is determined. The

TABLE 1B

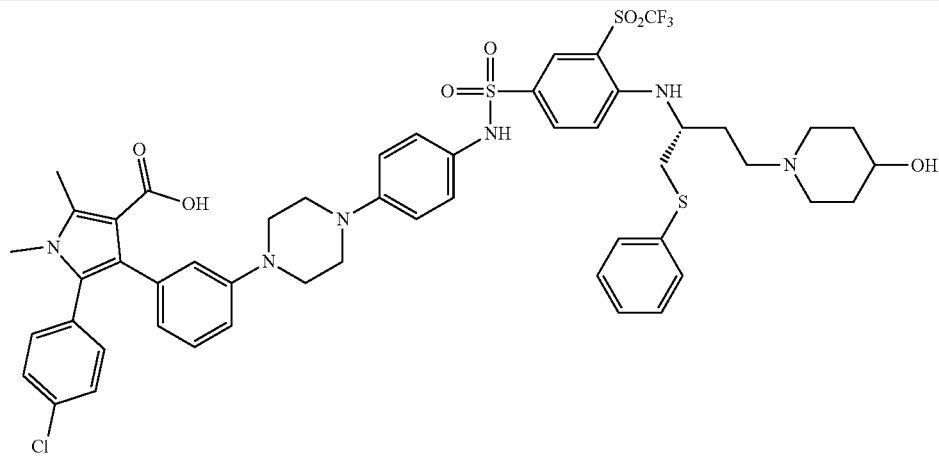

(R)-5-(4-chlorophenyl)-4-(3-(4-(4-((4-((4-(4-hydroxypiperidin-1-yl)-1-(phenylthio)butan-2-yl)amino)-3-((trifluoromethyl)sulfonyl)phenyl)sulfonamido)phenyl)piperazin-1-yl)phenyl)-1,2-dimethyl-1H-pyrrole-3-carboxylic acid

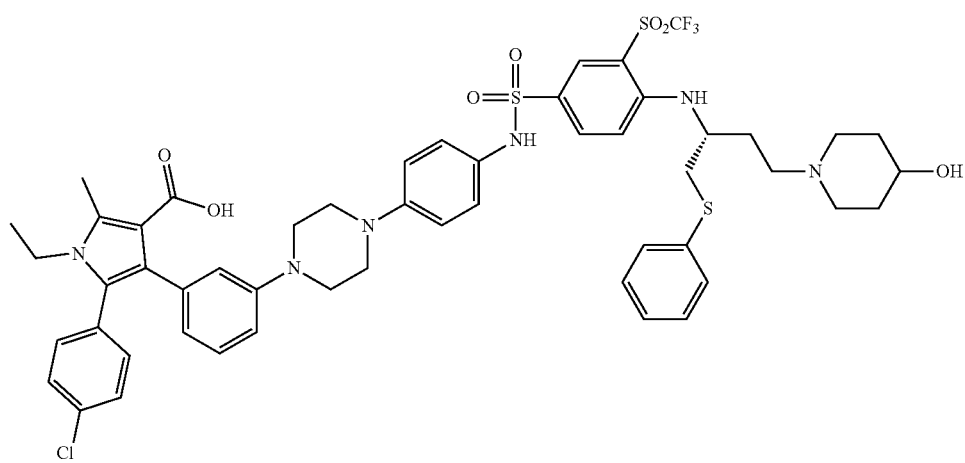

(R)-5-(4-chlorophenyl)-1-ethyl-4-(3-(4-(4-((4-((4-(4-hydroxypiperidin-1-yl)-1-(phenylthio)butan-2-yl)amino)-3-((trifluoromethyl)sulfonyl)phenyl)sulfonamido)phenyl)piperazin-1-yl)phenyl)-2-methyl-1H-pyrrole-3-carboxylic acid Evaluating Compounds for Senolytic and Chemotherapeutic Activity These and other compounds put forth in this disclosure can be evaluated on the molecular level for their ability to perform in a way that indicates they are candidate agents for use as active agents for the preparation of medicaments and use in human therapy.

For example, where the therapy includes triggering apoptosis of senescent cells by way of Bcl-2, Bcl-xL, Bcl-w, or other Bcl family protein, compounds can be tested for their ability to inhibit binding between one or more Bcl proteins and their respective cognate ligand. Example 1 provides an illustration of a homogeneous assay (an assay that does not require a separation step) for purposes of determining binding to the Bcl isoforms. Compounds can be screened on the molecular level for their ability to interact with the target isoform, thereby causing senolysis. Examples 2 and 3 provide illustrations of assays designed for this purpose.

ability of the compound to kill or inhibit senescent cells can be compared with the effect of the compound on normal cells that are freely dividing at low density, and normal cells that are in a quiescent state at high density. Examples 2 and 3 provide illustrations of senescent cell killing using the human target tissue fibroblast IMR90 cell line and HUVEC cells. Similar protocols are known and can be developed or optimized for testing the ability of the cells to kill or inhibit other senescent cells and other cell types, such as cancer cells.

Candidate Bcl inhibitors that are effective in selectively killing senescent cells in vitro can be further screened in animal models for particular disease. Examples 4, 5, 6, and 7 of the Experimental Section below provide illustrations for osteoarthritis, eye disease, lung disease, and atherosclerosis, respectively.

Alternatively or in addition, compounds can be evaluated for an ability to kill cancer or tumor cells specifically.

Cultured cells are contacted with the compound, and the degree of cytotoxicity for the cells, and/or the ability to inhibit cell proliferation is determined. The effect on cancer cells can be compared with the effect of the compound on normal cells of the same original tissue type in culture. The compounds can also be tested for their ability to remove tumors, to inhibit cancer cell growth, and to treat symptoms and signs of cancer in established animal models. Example 8 provides illustrations of in vitro and in vivo assays to assess the potential of the compounds in this disclosure as chemotherapeutic agents.

Formulation of Medicaments

Preparation and formulation of pharmaceutical agents for use according to this disclosure can incorporate standard technology, as described, for example, in the current edition of *Remington: The Science and Practice of Pharmacy*. The formulation will typically be optimized for administration to the target tissue, for example, by local administration, in a manner that enhances access of the active agent to the target senolytic cells and providing the optimal duration of effect, while minimizing side effects or exposure to tissues that are not involved in the condition being treated.

Pharmaceutical preparations for use in treating senescence-related conditions and other diseases can be prepared by mixing a Bcl inhibitor with a pharmaceutically acceptable base or carrier and as needed one or more pharmaceutically acceptable excipients. Depending on the target tissue, it may be appropriate to formulate the pharmaceutical composition for sustained or timed release. Oral timed release formulations may include a mixture of isomeric variants, binding agents, or coatings. Injectable time release formulations may include the active agent in combination with a binding agent, encapsulating agent, or microparticle. For treatment of joint diseases such as osteoarthritis, the pharmaceutical composition is typically formulated for intra-articular administration. For treatment of eye disease such as glaucoma, diabetic retinopathy or age-related macular degeneration (AMD), the composition may be formulated for intravitreal or intracameral administration. For treatment of lung diseases, the composition may be formulated as an aerosol, or for intratracheal administration.

This disclosure provides commercial products that are kits that enclose unit doses of one or more of the agents or compositions described in this disclosure. Such kits typically comprise a pharmaceutical preparation in one or more containers. The preparations may be provided as one or more unit doses (either combined or separate). The kit may contain a device such as a syringe for administration of the agent or composition in or around the target tissue of a subject in need thereof. The product may also contain or be accompanied by an informational package insert describing the use and attendant benefits of the drugs in treating the senescent cell associated condition, and optionally an appliance or device for therapeutic delivery of the composition.

Treatment Design

Senescent cells accumulate with age, which is why conditions mediated by senescent cells occur more frequently in older adults. In addition, different types of stress on pulmonary tissues may promote the emergence of senescent cells and the phenotype they express. Cell stressors include oxidative stress, metabolic stress, DNA damage (for example, as a result of environmental ultraviolet light exposure or genetic disorder), oncogene activation, and telomere shortening (resulting, for example, from hyperproliferation). Tissues that are subject to such stressors may have a higher prevalence of senescent cells, which in turn may lead to presentation of certain conditions at an earlier age, or in a more severe form. An inheritable susceptibility to certain conditions suggests that the accumulation of disease-mediating senescent cells may directly or indirectly be influenced by genetic components, which can lead to earlier presentation.

One of the benefits of the senescent cell paradigm is that successful removal of senescent cells may provide the subject with a long-term therapeutic effect. Senescent cells are essentially non-proliferative, which means that subsequent repopulation of a tissue with more senescent cells can only occur by conversion of non-senescent cells in the tissue to senescent cells—a process that takes considerably longer than simple proliferation. As a general principle, a period of therapy with a senolytic agent that is sufficient to remove senescent cells from a target tissue (a single dose, or a plurality of doses given, for example, every day, semi weekly, or weekly, given over a period of a few days, a week, or several months) may provide the subject with a period of efficacy (for example, for two weeks, a month, two months, or more) during which the senolytic agent is not administered, and the subject experiences alleviation, reduction, or reversal of one or more adverse signs or symptoms of the condition being treated.

To treat a particular senescence-related condition with a senolytic agent according to this disclosure, the therapeutic regimen will depend on the location of the senescent cells, and the pathophysiology of the disease.

Senescence-Related Conditions Suitable for Treatment

The Bcl inhibitors of this disclosure can be used for prevention or treatment of various senescence-related conditions. Such conditions will typically (although not necessarily) characterized by an overabundance of senescent cells (such as cells expressing p16 and other senescence markers) in or around the site of the condition, or an overabundance of expression of p16 and other senescence markers, in comparison with the frequency of such cells or the level of such expression in unaffected tissue. Non-limiting examples of current interest include the treatment of osteoarthritis, eye disease, and lung disease, as illustrated in the following sections.

Treatment of Osteoarthritis

Any of the Bcl inhibitors listed in this disclosure can be developed for treating osteoarthritis in accordance with this disclosure. Similarly, of the Bcl inhibitors listed in this disclosure can be developed for selectively eliminating senescent cells in or around a joint of a subject in need thereof, including but not limited to a joint affected by osteoarthritis.

Osteoarthritis degenerative joint disease is characterized by fibrillation of the cartilage at sites of high mechanical stress, bone sclerosis, and thickening of the synovium and the joint capsule. Fibrillation is a local surface disorganization involving splitting of the superficial layers of the cartilage. The early splitting is tangential with the cartilage surface, following the axes of the predominant collagen bundles. Collagen within the cartilage becomes disorganized, and proteoglycans are lost from the cartilage surface. In the absence of protective and lubricating effects of proteoglycans in a joint, collagen fibers become susceptible to degradation, and mechanical destruction ensues. Predisposing risk factors for developing osteoarthritis include increasing age, obesity, previous joint injury, overuse of the joint, weak thigh muscles, and genetics. Symptoms of osteoarthritis include sore or stiff joints, particularly the hips, knees, and lower back, after inactivity or overuse; stiffness after resting that goes away after movement; and pain that is worse after activity or toward the end of the day.

Compounds according to this disclosure can be used to reduce or inhibit loss or erosion of proteoglycan layers in a joint, reduces inflammation in the affected joint, and promotes, stimulates, enhances, or induces production of collagen, for example, type 2 collagen. The compound may causes a reduction in the amount, or level, of inflammatory cytokines, such as IL-6, produced in a joint and inflammation is reduced. The compounds can be used for treating osteoarthritis and/or inducing collagen, for example, Type 2 collagen, production in the joint of a subject. A compound also can be used for decreasing, inhibiting, or reducing production of metalloproteinase 13 (MMP-13), which degrades collagen in a joint, and for restoring proteoglycan layer or inhibiting loss and/or degradation of the proteoglycan layer. Treatment with a compound thereby may also reduce the likelihood of, inhibits, or decreases erosion, or slows erosion of the bone. The compound may be administered directly to an osteoarthritic joint, for example, intraarticularly, topically, transdermally, intradermally, or subcutaneously. The compound may also restore, improve, or inhibit deterioration of strength of a join, and reduce joint pain.

Treatment of Ophthalmic Conditions

Any of the Bcl inhibitors listed in this disclosure can be used for preventing or treating an ophthalmic condition in a subject in need thereof by removing senescent cells in or around an eye of the subject, whereby at least one sign or symptom of the disease is decreased in severity. Such conditions include both back-of-the-eye diseases, and front-of-the-eye diseases. Similarly, of the Bcl inhibitors listed in this disclosure can be developed for selectively eliminating senescent cells in or around ocular tissue in a subject in need thereof.

Diseases of the eye that can be treated according to this disclosure include presbyopia, macular degeneration (including wet or dry AMD), diabetic retinopathy, and glaucoma.

Macular degeneration is a neurodegenerative condition that can be characterized as a back-of-the-eye disease, It causes the loss of photoreceptor cells in the central part of retina, called the macula. Macular degeneration can be dry or wet. The dry form is more common than the wet, with about 90% of age-related macular degeneration (AMD) patients diagnosed with the dry form. Dry AMD is associated with atrophy of the retinal pigment epithelium (RPE) layer, which causes loss of photoreceptor cells. With wet AMD, new blood vessels may grow beneath the retina and leak blood and fluid. Abnormally leaky choroidal neovascularization can cause the retinal cells to die, creating blind spots in central vision. The formation of exudates, or "drusen," underneath the Bruch's membrane of the macula is can be a physical sign that macular degeneration is emerging. Symptoms of macular degeneration include, for example, perceived distortionand color perception changes.

Another back-of-the-eye disease is diabetic retinopathy (DR). According to Wikipedia, the first stage of DR is non-proliferative, and typically has no substantial symptoms or signs. NPDR is detectable by fundus photography, in which microaneurysms (microscopic blood-filled bulges in the artery walls) can be seen. If there is reduced vision, fluorescein angiography can be done to see the back of the eye. Narrowing or blocked retinal blood vessels can be seen clearly and this is called retinal ischemia (lack of blood flow). Macular edema in which blood vessels leak their contents into the macular region can occur at any stage of NPDR. The symptoms of macular edema are blurred vision and darkened or distorted images that are not the same in both eyes. Optical Coherence Tomography can show the areas of retinal thickening (due to fluid accumulation) of macular edema. In the second stage of DR, abnormal new blood vessels (neovascularization) form at the back of the eye as part of proliferative diabetic retinopathy (PDR), which may burst and bleed (vitreous hemorrhage) and blur the vision. On funduscopic exam, a clinician will see cotton wool spots, flame hemorrhages (similar lesions are also caused by the alpha-toxin of *Clostridium novyi*), and dot-blot hemorrhages.

Benefits of treatment of back-of-the-eye disease with a senolytic agent of this disclosure may include inhibition or delay of adverse features of the condition, such as abnormal neovascularization, pathogenic angiogenesis, vaso-obliteration, intraocular bleeding, retinal damage, and vision loss. The senolytic agent may be administered in or around the eye, for example, by intraocular, intravitreal, or retrobulbar injection. Optimally, there will be a reversal in some of the pathophysiology, such as restoration of functional vasculature, functional angiogenesis, retinal regrowth or restoration, with a partial degree of vision improvement.

Presbyopia is an age-related condition where the eye exhibits a progressively diminished ability to focus on near objects as the speed and amplitude of accommodation of a normal eye decreases with advancing age Loss of elasticity of the crystalline lens and loss of contractility of the ciliary muscles can cause presbyopia. Age-related changes in the mechanical properties of the anterior lens capsule and posterior lens capsule suggest that the mechanical strength of the posterior lens capsule decreases significantly with age as a consequence of change in the composition of the tissue. The major structural component of the lens capsule is basement membrane type IV collagen that is organized into a three-dimensional molecular network. Adhesion of the collagen IV, fibronectin, and lamina to the intraocular lens can inhibit cell migration and can reduce the risk of PCO.

Senolytic agents provided by this disclosure may slow the disorganization of the type IV collagen network, decrease or inhibit epithelial cell migration and can also delay the onset of presbyopia or decrease or slow the progressive severity of the condition. They can also be useful for post-cataract surgery to reduce the likelihood of occurrence of PCO.

Glaucoma and other front-of-the-eye diseases may also be amenable to treatment with the senolytic agents provided in this disclosure. Normally, clear fluid flows into and out of the front part of the eye, known as the anterior chamber. In individuals who have open/wide-angle glaucoma, the clear fluid drains too slowly, leading to increased pressure within the eye. If left untreated, the high pressure in the eye can subsequently damage the optic nerve and can lead to complete blindness. The loss of peripheral vision is caused by the death of ganglion cells in the retina.

Possible benefits of therapy include a reduction in intraocular pressure, improved draining of ocular fluid through the trabecular network, and an inhibition or delay of vision loss that results. The senolytic agent may be administered in or around the eye, for example, by intraocular or intracameral injection or in a topical formulation. The effect of therapy can be monitored by automated perimetry, gonioscopy, imaging technology, scanning laser tomography, HRT3, laser polarimetry, GDX, ocular coherence tomography, ophthalmoscopy, and pachymeter measurements that determine central corneal thickness.

Treatment of Pulmonary Conditions

Any of the Bcl inhibitors listed in this disclosure can be developed for treating pulmonary disease in accordance with this disclosure. Similarly, of the Bcl inhibitors listed in this disclosure can be developed for selectively eliminating senescent cells in or around a lung of a subject in need thereof. Pulmonary conditions that can be treated include idiopathic pulmonary fibrosis (IPF), chronic obstructive pulmonary disease (COPD), asthma, cystic fibrosis, bronchiectasis, and emphysema.

COPD is a lung disease defined by persistently poor airflow resulting from the breakdown of lung tissue, emphysema, and the dysfunction of the small airways, obstructive bronchiolitis. Primary symptoms of COPD include shortness of breath, wheezing, chest tightness, chronic cough, and excess sputum production. Elastase from cigarette smoke-activated neutrophils and macrophages can disintegrate the extracellular matrix of alveolar structures, resulting in enlarged air spaces and loss of respiratory capacity. COPD can be caused by, for example, tobacco smoke, cigarette smoke, cigar smoke, secondhand smoke, pipe smoke, occupational exposure, exposure to dust, smoke, fumes, and pollution, occurring over decades thereby implicating aging as a risk factor for developing COPD.

The processes that cause lung damage include, for example, oxidative stress produced by the high concentrations of free radicals in tobacco smoke, cytokine release due to the inflammatory response to irritants in the airway, and impairment of anti-protease enzymes by tobacco smoke and free radicals, allowing proteases to damage the lungs. Genetic susceptibility can also contribute to the disease. In about 1% percent of people with COPD, the disease results from a genetic disorder that causes low level production of alpha-1-antitrypsin in the liver. Alpha-1-antitrypsin is normally secreted into the bloodstream to help protect the lungs.

Pulmonary fibrosis is a chronic and progressive lung disease characterized by stiffening and scarring of the lung, which can lead to respiratory failure, lung cancer, and heart failure. Fibrosis is associated with repair of epithelium. Fibroblasts are activated, production of extracellular matrix proteins is increased, and transdifferentiation to contractile myofibroblasts contribute to wound contraction. A provisional matrix plugs the injured epithelium and provides a scaffold for epithelial cell migration, involving an epithelial-mesenchymal transition (EMT). Blood loss associated with epithelial injury induces platelet activation, production of growth factors, and an acute inflammatory response. Normally, the epithelial barrier heals and the inflammatory response resolves. However, in fibrotic disease the fibroblast response continues, resulting in unresolved wound healing. Formation of fibroblastic foci is a feature of the disease, reflecting locations of ongoing fibrogenesis.

Subjects at risk of developing pulmonary fibrosis include, for example, subjects who have been exposed to environmental or occupational pollutants, such as asbestosis and silicosis; those who smoke cigarettes; those who have a connective tissue diseases such as RA, SLE, scleroderma, sarcoidosis, or Wegener's granulomatosis; those who have infections; those who take certain medications, including, for example, amiodarone, bleomycin, busufan, methotrexate, and nitrofurantoin; those subject to radiation therapy to the chest; and those whose family member have pulmonary fibrosis.

Other pulmonary conditions that can be treated by using a compound according to this condition include emphysema, asthma, bronchiectasis, and cystic fibrosis. Pulmonary diseases can also be exacerbated by tobacco smoke, occupational exposure to dust, smoke, or fumes, infection, or pollutants that contribute to inflammation.

Symptoms of lung disease can include of shortness of breath, wheezing, chest tightness, having to clear one's throat first thing in the morning because of excess mucus in the lungs, a chronic cough that produces sputum that can be clear, white, yellow or greenish, cyanosis, frequent respiratory infections, lack of energy, and unintended weight loss. Symptoms of pulmonary fibrosis may include shortness of breath, particularly during exercise; dry, hacking cough; fast, shallow breathing; gradual, unintended weight loss; fatigue; aching joints and muscles; and clubbing of the fingers or toes.

Lung function before, during, and after treatment can be determined, for example, by measuring expiratory reserve volume (ERV), forced vital capacity (FVC), forced expiratory volume (FEV), total lung capacity (TLC), vital capacity (VC), residual volume (RV), and functional residual capacity (FRC). Gas exchange across alveolar capillary membrane can be measured using diffusion capacity for carbon monoxide (DLCO). Exercise capacity can be measured as a proxy. Peripheral capillary oxygen saturation ($SpO_2$) can also be measured: normal oxygen levels are typically between 95% and 100%, An $SpO_2$ level below 90% suggests the subject has hypoxemia. Values below 80% are considered critical and require intervention to maintain brain and cardiac function and avoid cardiac or respiratory arrest.

Benefits of treatment may include inhibiting progression or reversing of any of these effects. Administration of the senolytic agent may be systemic, or local at a site in or around the lung: for example, by inhalation as an aerosol or powder, or by intubation. Optimally, the agent will improve the $SpO_2$ level and exercise capacity.

Treatment of Atherosclerosis

Senolytic compounds can be used for the treatment of atherosclerosis: for example, by inhibiting formation, enlargement, or progression of atherosclerotic plaques in a subject. The senolytic compounds can also be used to enhance stability of atherosclerotic plaques that are present in one or more blood vessels of a subject, thereby inhibiting them from rupturing and occluding the vessels.

Atherosclerosis is characterized by patchy intimal plaques, atheromas, that encroach on the lumen of medium-sized and large arteries; the plaques contain lipids, inflammatory cells, smooth muscle cells, and connective tissue. Atherosclerosis can affect large and medium-sized arteries, including the coronary, carotid, and cerebral arteries, the aorta and branches thereof, and major arteries of the extremities.

Atherosclerosis may lead to an increase in artery wall thickens. Symptoms develop when growth or rupture of the plaque reduces or obstructs blood flow; and the symptoms can vary depending on which artery is affected. Atherosclerotic plaques can be stable or unstable. Stable plaques regress, remain static, or grow slowly, sometimes over several decades, until they can cause stenosis or occlusion. Unstable plaques are vulnerable to spontaneous erosion, fissure, or rupture, causing acute thrombosis, occlusion, and infarction long before they cause hemodynamically significant stenosis. Clinical events can result from unstable plaques, which do not appear severe on angiography; thus, plaque stabilization can be a way to reduce morbidity and mortality. Plaque rupture or erosion can lead to major cardiovascular events such as acute coronary syndrome and stroke. Disrupted plaques can have a greater content of lipid, macrophages, and have a thinner fibrous cap than intact plaques.

Diagnosis of atherosclerosis and other cardiovascular disease can be based on symptoms, for example, angina, chest pressure, numbness or weakness in arms or legs, difficulty speaking or slurred speech, drooping muscles in face, leg pain, high blood pressure, kidney failure and/or erectile dysfunction, medical history, and/or physical examination of a patient. Diagnosis can be confirmed by angiography, ultrasonography, or other imaging tests. Subjects at risk of developing cardiovascular disease include those having any one or more of predisposing factors, such as a family history of cardiovascular disease and those having other risk factors, for example, predisposing factors including high blood pressure, dyslipidemia, high cholesterol, diabetes, obesity and cigarette smoking, sedentary lifestyle, and hypertension. The condition can be assessed, for example, by angiography, electrocardiography, or stress test.

Potential benefits of treatment with a senolytic agent include alleviating or halting progression of one or more signs or symptoms of the condition, such as the frequency of plaques, the surface area of vessels covered by plaques, angina, and reduced exercise tolerance.

Definitions

A "senescent cell" is generally thought to be derived from a cell type that typically replicates, but as a result of aging or other event that causes a change in cell state, can no longer replicate. Depending on the context, senescent cells can be identified as expressing p16, or at least one marker selected from p16, senescence-associated β-galactosidase, and lipofuscin; sometimes two or more of these markers, and other markers of the senescence-associated secretory profile (SASP) such as but not limited to interleukin 6, and inflammatory, angiogenic and extracellular matrix modifying proteins. Unless explicity stated otherwise, the senescent cells referred to in the claims do not include cancer cells.

A "senescence associated", "senescence related" or "age related" disease, disorder, or condition is a physiological condition that presents with one or more symptoms or signs that are adverse to the subject. The condition is "senescence associated" if it is "caused or mediated at least in part by senescent cells." This means that at least one component of the SASP in or around the affected tissue plays a role in the pathophysiology of the condition such that elimination of at least some of the senescent cells in the affected tissue results in substantial relief or lessening of the adverse symptoms or signs, to the patient's benefit. Senescence associated disorders that can potentially be treated or managed using the methods and products according to this disclosure include disorders referred to in this disclosure and in previous disclosures referred to in the discussion. Unless explicitly stated otherwise, the term does not include cancer.

An inhibitor of protein function or Bcl function is a compound that to a substantial degree prevents the target protein already expressed in a target cell from performing an enzymatic, binding, or regulatory function that the protein or Bcl family member normally performs in the target cell. This results in elimination of the target cell or rendering the cell more susceptible to the toxicity of another compound or event. A compound qualifies as a "Bcl inhibitor" or a compound that "inhibits Bcl activity" in this disclosure if it has an $IC_{50}$ when tested in an assay according to Example 1 below that is less than 1,000 nM (1.0 µM). Activity that is less than 100 nM or 10 nM, or between 100 nM and 1 nM is often preferred, depending on the context.

The term "Bcl" or "Bcl protein" refers to the family of Bcl proteins, exemplified by Bcl-2, Bcl-xL, and Bcl-w. A Bcl inhibitor of this disclosure will be able to inhibit at least one of Bcl-2, Bcl-xL, and Bcl-w. Typically but not necessarily, an inhibitor of one of these Bcl proteins will to some extent inhibit the other two. The compounds provided in this disclosure can be tested for activity of any Bcl family members, to identify compounds that have inhibitory activity and are potentially specific for Bcl-2, Bcl-xL, or Bcl-w. Such an inhibitor will have an $IC_{50}$ for a target Bcl from this list that is at least 10-fold better than its $IC_{50}$ for the other two Bcl family members on the list.

A compound, composition or agent is typically referred to as "senolytic" if it eliminates senescent cells, in preference replicative cells of the same tissue type, or quiescent cells lacking SASP markers. Alternatively or in addition, a compound or combination may effectively be used if it decreases the release of pathological soluble factors or mediators as part of the senescence associated secretory phenotype that play a role in the initial presentation or ongoing pathology of a condition, or inhibit its resolution. In this respect, the term "senolytic" refers to functional inhibition, such that compounds that work primarily by inhibiting rather than eliminating senescent cells (senescent cell inhibitors) can be used in a similar fashion with ensuing benefits. Model senolytic compositions and agents in this disclosure have an $EC_{50}$ when tested in an assay according to Example 2 below that is less than 1 µM. Activity that is less than 0.1 µM, or between 1 µM and 0.1 µM may be preferred. The selectivity index (SI) ($EC_{50}$ of senescent cells compared with non-senescent cells of the same tissue type) may be better than 1, 2, 5, or 10, depending on the context.

Selective removal or "elimination" of senescent cells from a mixed cell population or tissue doesn't require that all cells bearing a senescence phenotype be removed: only that the proportion of senescent cells initially in the tissue that remain after treatment is substantially higher than the proportion of non-senescent cells initially in the tissue that remain after the treatment.

Successful "treatment" of a condition according to this disclosure may have any effect that is beneficial to the subject being treated. This includes decreasing severity, duration, or progression of a condition, or of any adverse signs or symptoms resulting therefrom. Treatment may also be unsuccessful, resulting in no improvement in typical signs and symptoms of the condition. A concurrent objective of therapy is to minimize adverse effects on the target tissue or elsewhere in the treated subject. In some circumstances, senolytic agents can also be used to prevent or inhibit presentation of a condition for which a subject is susceptible, for example, because of an inherited susceptibility of because of medical history.

A "therapeutically effective amount" is an amount of a compound of the present disclosure that (i) treats the particular disease, condition, or disorder, (ii) attenuates, ameliorates, or eliminates one or more symptoms of the particular disease, condition, or disorder, (iii) prevents or delays the onset of one or more symptoms of the particular disease, condition, or disorder described herein, (iv) prevents or delays progression of the particular disease, condition or disorder, or (v) at least partially reverses damage caused by the condition prior to treatment.

A "phosphorylated" form of a compound is a compound which bears one or more phosphate groups covalently bound to the core structure through an oxygen atom, which was typically but not necessarily present on the molecule before phosphorylation. For example, one or more —OH or —COOH groups may have been substituted in place of the hydrogen with a phosphate group which is either —OPO$_3$H$_2$ or —C$_n$PO$_3$H$_2$ (where n is 1 to 4). In some phosphorylated forms, the phosphate group may be removed in vivo (for example, by enzymolysis), in which case the phosphorylated form may be a pro-drug of the non-phosphorylated form. A non-phosphorylated form has no such phosphate group. A dephosphorylated form is a derivative of a phosphorylated molecule after at least one phosphate group has been removed.

"Small molecule" Bcl inhibitors according to this disclosure have molecular weights less than 20,000 daltons, and are often less than 10,000, 5,000, or 2,000 daltons. Small molecule inhibitors are not antibody molecules or oligonucleotides, and typically have no more than five hydrogen bond donors (the total number of nitrogen—hydrogen and oxygen—hydrogen bonds), and no more than 10 hydrogen bond acceptors (all nitrogen or oxygen atoms).

"Prodrug" refers to a derivative of an active agent that requires a transformation within the body to release the active agent. The transformation can be an enzymatic transformation. Sometimes, the transformation is a cyclization transformation, or a combination of an enzymatic transformation and a cyclization transformation. Prodrugs are frequently, although not necessarily, pharmacologically inactive until converted to the active agent.

Unless otherwise stated or required, each of the compound structures referred to in the disclosure include conjugate acids and bases having the same structure, crystalline and amorphous forms of those compounds, pharmaceutically acceptable salts, and prodrugs. This includes, for example, polymorphs, solvates, hydrates, unsolvated polymorphs (including anhydrates), and phosphorylated and unphosphorylated forms of the compounds.

INCORPORATION BY REFERENCE

For all purposes in the United States and in other jurisdictions where effective, each and every publication and patent document cited in this disclosure is hereby incorporated herein by reference in its entirety for all purposes to the same extent as if each such publication or document was specifically and individually indicated to be incorporated herein by reference.

U.S. Pat. No. 10,130,628 (Laberge et al.) and US 20170266211 A1 (David et al.) are hereby incorporated herein for all purposes, including but not limited to the identification and formulation of senolytic agents, and their use for treating various conditions thought to be mediated at least in part by senescent cells. U.S. Pat. Nos. 8,691,184, 9,096,625, and 9,403,856 (Wang et al.) are hereby incorporated herein by reference in its entirety for all purposes, including the features of compounds in the Bcl library, their preparation and use. U.S. patent application Ser. No. 15/675,171 (filed Aug. 11, 2017) and 62/579,793 (filed Oct. 31, 2017) are hereby incorporated herein for all purposes, including but not limited to the identification, formulation, and use of compounds capable of eliminating or reducing the activity of senescent cells and treating various ophthalmic conditions.

EXAMPLES

Example 1: Measuring Bcl Inhibition

The ability of candidate compounds to inhibit Bcl-2 and Bcl-xL activity can be measured on the molecular level by direct binding. This assay uses a homogenous assay technology based on oxygen channeling that is marketed by PerkinElmer Inc., Waltham, Mass.: see Eglin et al., Current Chemical Genomics, 2008, 1, 2-10. The test compound is combined with the target Bcl protein and a peptide representing the corresponding cognate ligand, labeled with biotin. The mixture is then combined with streptavidin bearing luminescent donor beads and luminescent acceptor beads, which proportionally reduces luminescence if the compound has inhibited the peptide from binding to the Bcl protein.

Bcl-2, Bcl-xL and Bcl-w are available from Sigma-Aldrich Co., St. Louis, Mo. Biotinylated BIM peptide (ligand for Bcl-2) and BAD peptide (ligand for Bcl-xL) are described in US 2016/0038503 A1. AlphaScreen® Streptavidin donor beads and Anti-6×His AlphaLISA® acceptor beads are available from PerkinElmer.

To conduct the assay, a 1:4 dilution series of the compound is prepared in DMSO, and then diluted 1:100 in assay buffer. In a 96-well PCR plate, the following are combined in order: 10 µL peptide (120 nM BIM or 60 nM BIM), 10 µL test compound, and 10 µL Bcl protein (0.8 nM Bcl-2/W or 0.4 nM Bcl-XL). The assay plate is incubated in the dark at room temperature for 24 h. The next day, donor beads and acceptor beads are combined, and 5 µL is added to each well. After incubating in the dark for 30 minute, luminescence is measured using a plate reader, and the affinity or degree of inhibition by each test compound is determined.

Example 2: Measuring Senolytic Activity in Fibroblasts

Human fibroblast IMR90 cells can be obtained from the American Type Culture Collection (ATCC®) with the designation CCL-186. The cells are maintained at <75% confluency in DMEM containing FBS and Pen/Strep in an atmosphere of 3% O2, 10% $CO_2$, and ~95% humidity. The cells are divided into groups: irradiated cells (cultured for 14 days after irradiation prior to use) and quiescent cells (cultured at high density for four day prior to use).

On day 0, the irradiated cells are prepared as follows. IMR90 cells are washed, placed in T175 flasks at a density of 50,000 cells per mL, and irradiated at 10-15 Gy. Following irradiation, the cells are plated at 100 µL in 96-well plates. On days 1, 3, 6, 10, and 13, the medium in each well is aspirated and replaced with fresh medium.

On day 10, the quiescent healthy cells are prepared as follows. IMR90 cells are washed, combined with 3 mL of TrypLE trypsin-containing reagent (Thermofisher Scientific, Waltham, Mass.) and cultured for 5 min until the cells have rounded up and begin to detach from the plate. Cells are dispersed, counted, and prepared in medium at a concentration of 50,000 cells per mL. 100 µL of the cells is plated in each well of a 96-well plate. Medium is changed on day 13. On day 14, test inhibitor compounds are combined with the cells as follows. A DMSO dilution series of each test compound is prepared at 200 times the final desired concentration in a 96-well PCR plate. Immediately before use, the DMSO stocks are diluted 1:200 into prewarmed complete medium. Medium is aspirated from the cells in each well, and 100 µL/well of the compound containing medium is added.

Candidate senolytic agents for testing are cultured with the cells for 6 days, replacing the culture medium with fresh medium and the same compound concentration on day 17. Bcl 2 inhibitors are cultured with the cells for 3 days. The assay system uses the properties of a thermostable luciferase to enable reaction conditions that generate a stable luminescent signal while simultaneously inhibiting endogenous ATPase released during cell lysis. At the end of the culture period, 100 µL of CellTiter-Glo® reagent (Promega Corp., Madison, Wis.) is added to each of the wells. The cell plates are placed for 30 seconds on an orbital shaker, and luminescence is measured.

Example 3: Measuring Senolytic Activity in HUVEC Cells and Other Senescent Cells Human umbilical vein (HUVEC) cells from a single lot were expanded in Vascular Cell Basal Media supplemented with the Endothelial Cell Growth Kit™-VEGF from ATCC to approximately eight population doublings then cryopreserved. Nine days prior to the start of the assay, cells for the senescent population were thawed and seeded at approximately 27,000/$cm_2$. All cells were cultured in humidified incubators with 5% $CO_2$ and 3% $O_2$ and media was changed every 48 hr. Two days after seeding, the cells were irradiated, delivering 12 Gy radiation from an X-ray source. Three days prior to the start of the assay, cells for the non-senescent populations are thawed and seeded as for the senescent population. One day prior to the assay, all cells were trypsinized and seeded into 384-well plates, 5,000/well senescent cells and 10,000/well non-senescent in separate plates in a final volume of 55 µL/well. In each plate, the central 308 wells contained cells and the outer perimeter of wells was filled with 70 µL/well deionized water.

On the day of the assay, compounds were diluted from 10 mM stocks into media to provide the highest concentration working stock, aliquots of which were then further diluted in media to provide the remaining two working stocks. To initiate the assay, 5 µL of the working stock was added to the cell plates. The final test concentrations were 20, 2, and 0.2 µM. In each plate, 100 test compounds were assayed in triplicate at a single concentration along with a three wells of a positive control and five no treatment (DMSO) controls. Following compound addition, the plates are returned to the incubators for three days.

Cell survival was assessed indirectly by measuring total ATP concentration using CellTiter-Glo™ reagent (Promega). The resultant luminescence was quantitated with an EnSpire™ plate reader (Perkin Elmer). The relative cell viability for each concentration of a compound was calculated as a percentage relative to the no-treatment controls for the same plate.

For follow-up dose responses of potential lead compounds, 384-well plates of senescent and non-senescent cells were prepared as described above. Compounds were prepared as 10-point 1:3 dilution series in DMSO, then diluted to 12× in media. Five microliters of this working stock was then added to the cell plates. After three days of incubation, cell survival relative to DMSO control was calculated as described above. All measurements were performed in quadruplicate.

Other cell lines and primary cell cultures may be used as an alternative to IMR90 fibroblasts or HUVEC cells that align with the intended target tissue in vivo. An example is the use of cultured human retinal microvascular endothelial cells (HRMEC) for screening compounds intended for treatment of eye disease. The cells are cultured according to known protocols for the chosen cell line, and irradiated in a similar fashion to render them senescent.

Example 4: Efficacy of Senolytic Agents in an Osteoarthritis Model

This example illustrates the testing of an MDM2 inhibitor in a mouse model for treatment of osteoarthritis. It can be adapted mutatis mutandis to test and develop Bcl inhibitors for use in clinical therapy.

The model was implemented as follows. C57BL/6J mice underwent surgery to cut the anterior cruciate ligament of one rear limb to induce osteoarthritis in the joint of that limb. During week 3 and week 4 post-surgery, the mice were treated with 5.8 µg of Nutlin-3A (n=7) per operated knee by intra-articular injection, q.o.d. for 2 weeks. At the end of 4 weeks post-surgery, joints of the mice were monitored for presence of senescent cells, assessed for function, monitored for markers of inflammation, and underwent histological assessment.

Two control groups of mice were included in the studies performed: one group comprising C57BL/6J or 3MR mice that had undergone a sham surgery (n=3) (i.e., surgical procedures followed except for cutting the ACL) and intra-articular injections of vehicle parallel to the GCV (ganciclovir) treated group; and one group comprising C57BL/6J or 3MR mice that had undergone an ACL surgery and received intra-articular injections of vehicle (n=5) parallel to the GCV-treated group. RNA from the operated joints of mice from the Nutlin-3A treated mice was analyzed for expression of SASP factors (mmp3, IL-6) and senescence markers (p16). qRT-PCR was performed to detect mRNA levels.

FIGS. 2A, 2B, and 2C show expression of p16, IL-6, and MMP13 in the tissue, respectively. The OA inducing surgery was associated with increased expression of these markers. Treatment with Nutlin-3A reduced the expression back to below the level of the controls. Treatment with Nutlin-3A cleared senescent cells from the joint.

Function of the limbs was assessed 4 weeks post-surgery by a weight bearing test to determine which leg the mice favored. The mice were allowed to acclimate to the chamber on at least three occasions prior to taking measurements. Mice were maneuvered inside the chamber to stand with one hind paw on each scale. The weight that was placed on each hind limb was measured over a three second period. At least three separate measurements were made for each animal at each time point. The results were expressed as the percentage of the weight placed on the operated limb versus the contralateral unoperated limb.

FIG. 3A shows the results of the functional study. Untreated mice that underwent osteoarthritis inducing surgery favored the unoperated hind limb over the operated hind limb (Δ). However, clearing senescent cells with Nutlin-3A abrogated this effect in mice that have undergone surgery (∇).

FIGS. 3B, 3C, and 3D show histopathology of joint tissue from these experiments. Osteoarthritis induced by ACL surgery caused the proteoglycan layer was destroyed. Clearing of senescent cells using Nutlin-3A completely abrogated this effect.

Example 5: Efficacy of Senolytic Agents in Models for Diabetic Retinopathy

This example illustrates the testing of a Bcl inhibitor in a mouse model for treatment of a back-of-the eye disease, specifically diabetic retinopathy. It can be adapted mutatis mutandis to test senolytic agents for use in clinical therapy.

The efficacy of model compound UBX1967 (a Bcl-xL inhibitor) was studied in the mouse oxygen-induced retinopathy (OIR) model (Scott and Fruttiger, Eye (2010) 24, 416-421, Oubaha et al, 2016). C57Bl/6 mouse pups and their CD1 foster mothers were exposed to a high oxygen environment (75% O2) from postnatal day 7 (P7) to P12. At P12, animals were injected intravitreally with 1 µl test compound (200, 20, or 2 uM) formulated in 1% DMSO, 10% Tween- 80, 20% PEG-400, and returned to room air until P17. Eyes were enucleated at P17 and retinas dissected for either vascular staining or qRT-PCR. To determine avascular or neovascular area, retinas were flat-mounted, and stained with isolectin B4 (IB4) diluted 1:100 in 1 mM $CaCl_2$. For quantitative measurement of senescence markers (e.g., Cdkn2a, Cdkn1a, Il6, Vegfa), qPCR was performed. RNA was isolated and cDNA was generated by reverse-transcription, which was used for qRT-PCR of the selected transcripts.

FIGS. 4A and 4B show that intravitreal ITT) administration UBX1967 resulted in statistically significant improvement in the degree of neovascularization and vaso-obliteration at all dose levels.

The efficacy of UBX1967 was also studied in the streptozotocin (STZ) model. C57BL/6J mice of 6- to 7-week were weighted and their baseline glycemia was measured (Accu-Chek™ Roche). Mice were injected intraperitoneally with STZ (Sigma-Alderich, St. Louis, Mo.) for 5 consecutive days at 55 mg/Kg. Age-matched controls were injected with buffer only. Glycemia was measured again a week after the last STZ injection and mice were considered diabetic if their non-fasted glycemia was higher than 17 mM (300 mg/L). STZ treated diabetic C57BL/6J mice were intravitreally injected with 1 µl of UBX1967 (2 µM or 20 µM, formulated as a suspension in 0.015% polysorbate-80, 0.2% Sodium Phosphate, 0.75% Sodium Chloride, pH 7.2) at 8 and 9 weeks after STZ administration. Retinal Evans blue permeation assay was performed at 10 weeks after STZ treatment.

FIGS. 4C and 4D show results for this protocol. Retinal and choroidal vascular leakage after intravitreal (IVT) administration UBX1967 improved in vascular permeability at both dose levels.

Other models of retinal ganglion cell damage can be used in testing that are relevant to glaucoma, where increased intraocular pressure (IOP) is thought to cause retinal ganglion cell loss and optic nerve damage. In preclinical species, increased anterior chamber pressure can result in retinal neuron loss as reported in several established models, including the magnetic microbead occlusion (Ito et al., Vis Exp. 2016 (109): 53731) and other glaucoma models (Almasieh and Levin, Annu Rev Vis Sci. 2017). Additionally, ischemia-reperfusion has been demonstrated to cause retinal injury which may result in cellular senescence. Presence of retinal senescence in such models can be used to monitor the impact of senolysis after intravitreal injection of test compounds.

Example 6: Efficacy of Senolytic Agents in a Pulmonary Disease Model

This example illustrates the testing of inhibitors in a mouse model for treatment of lung disease: specifically, a model for idiopathic pulmonary fibrosis (IPF). It can be adapted mutatis mutandis to test and develop Bcl inhibitors for use in clinical therapy.

As a model for chronic obstructive pulmonary disease (COPD), mice were exposed to cigarette smoke.

The effect of a senolytic agent on the mice exposed to smoke is assessed by senescent cell clearance, lung function, and histopathology.

The mice used in this study include the 3MR strain, described in US 2017/0027139 A1 and in Demaria et al., Dev Cell. 2014 Dec. 22; 31(6): 722-733. The 3MR mouse has a transgene encoding thymidine kinase that converts the prodrug ganciclovir (GCV) to a compound that is lethal to cells. The enzyme in the transgene is placed under control of the p16 promoter, which causes it to be specifically expressed in senescent cells. Treatment of the mice with GCV eliminates senescent cells.

Other mice used in this study include the INK-ATTAC strain, described in US 2015/0296755 A1 and in Baker et al., Nature 2011 Nov. 2; 479(7372):232-236. The INK-ATTAC mouse has a transgene encoding switchable caspase 8 under control of the p16 promoter. The caspase 8 can be activated by treating the mice with the switch compound AP20187, whereupon the caspase 8 directly induces apoptosis in senescent cells, eliminating them from the mouse.

To conduct the experiment, six-week-old 3MR (n=35) or INK-ATTAC (n=35) mice were chronically exposed to cigarette smoke generated from a Teague TE-10 system, an automatically-controlled cigarette smoking machine that produces a combination of side-stream and mainstream cigarette smoke in a chamber, which is transported to a collecting and mixing chamber where varying amounts of air is mixed with the smoke mixture. The COPD protocol was adapted from the COPD core facility at Johns Hopkins University (Rangasamy et al., 2004, J. Clin. Invest. 114: 1248-1259; Yao et al., 2012, J. Clin. Invest. 122:2032-2045).

Mice received a total of 6 hours of cigarette smoke exposure per day, 5 days a week for 6 months. Each lighted cigarette (3R4F research cigarettes containing 10.9 mg of total particulate matter (TPM), 9.4 mg of tar, and 0.726 mg of nicotine, and 11.9 mg carbon monoxide per cigarette [University of Kentucky, Lexington, Ky.]) was puffed for 2 seconds and once every minute for a total of 8 puffs, with the flow rate of 1.05 L/min, to provide a standard puff of 35 cm3. The smoke machine was adjusted to produce a mixture of side stream smoke (89%) and mainstream smoke (11%) by smoldering 2 cigarettes at one time. The smoke chamber atmosphere was monitored for total suspended particulates (80-120 mg/m3) and carbon monoxide (350 ppm).

Beginning at day 7, (10) INK-ATTAC and (10) 3MR mice were treated with AP20187 (3× per week) or ganciclovir (5 consecutive days of treatment followed by 16 days off drug, repeated until the end of the experiment), respectively. An equal number of mice received the corresponding vehicle. The remaining 30 mice (15 INK-ATTAC and 15 3MR) were evenly split with 5 of each genetically modified strain placed into three different treatment groups. One group (n=10) received Nutlin-3A (25 mg/kg dissolved in 10% DMSO/3% Tween-20™ in PBS, treated 14 days consecutively followed by 14 days off drug, repeated until the end of the experiment). One group (n=10) received ABT-263 (Navitoclax) (100 mg/kg dissolved in 15% DMSO/5% Tween-20, treated 7 days consecutively followed by 14 days off drug, repeated until the end of the experiment), and the last group (n=10) received only the vehicle used for ABT-263 (15% DMSO/ 5% Tween-20), following the same treatment regimen as ABT-263. An additional 70 animals that did not receive exposure to cigarette smoke were used as controls for the experiment.

After two months of cigarette smoke (CS) exposure, lung function was assessed by monitoring oxygen saturation using the MouseSTAT PhysioSuite™ pulse oximeter (Kent Scientific). Animals were anesthetized with isoflurane (1.5%) and the toe clip was applied. Mice were monitored for 30 seconds and the average peripheral capillary oxygen saturation (SpO2) measurement over this duration was calculated.

FIG. 5 shows the results. Clearance of senescent cells via AP2018, ganciclovir, ABT-263 (Navitoclax), or Nutlin-3A resulted in statistically significant increases in SpO2 levels in mice after two months of cigarette smoke exposure, compared with untreated controls.

Example 7: Efficacy of Senolytic Agents in Atherosclerosis when Administered Systemically This example illustrates the testing of an MDM2 inhibitor in a mouse model for treatment of atherosclerosis. The test compounds are administered systemically rather than locally. The model is done in an LDLR−/− strain of mice, which are deficient in the receptor for low-density lipoprotein. The experiments described here can be adapted mutatis mutandis to test and develop other types of inhibitors for use in clinical therapy.

Two groups of LDLR−/− mice (10 weeks) are fed a high fat diet (HFD) (Harlan Teklad TD.88137) having 42% calories from fat, beginning at Week 0 and throughout the study. Two groups of LDLR−/− mice (10 weeks) are fed normal chow (−HFD). From weeks 0-2, one group of HFD mice and —HFD mice are treated with Nutlin-3A (25 mg/kg, intraperitoneally). One treatment cycle is 14 days treatment, 14 days off. Vehicle is administered to one group of HFD mice and one group of −HFD mice. At week 4 (timepoint 1), one group of mice are sacrificed and to assess presence of senescent cells in the plaques. For the some of the remaining mice, Nutlin-3A and vehicle administration is repeated from weeks 4-6. At week 8 (timepoint 2), the mice are sacrificed and to assess presence of senescent cells in the plaques. The remaining mice are treated with Nutlin-3A or vehicle from weeks 8-10. At week 12 (timepoint 3), the mice are sacrificed and to assess the level of plaque and the number of senescent cells in the plaques.

Plasma lipid levels were measured in LDLR−/− mice fed a HFD and treated with Nutlin-3A or vehicle at timepoint 1 as compared with mice fed a —HFD (n=3 per group). Plasma was collected mid-afternoon and analyzed for circulating lipids and lipoproteins.

At the end of timepoint 1, LDLR−/− mice fed a HFD and treated with Nutlin-3A or vehicle were sacrificed (n=3, all groups), and the aortic arches were dissected for RT-PCR analysis of SASP factors and senescent cell markers. Values were normalized to GAPDH and expressed as fold-change versus age-matched, vehicle-treated LDLR−/− mice on a normal diet. The data show that clearance of senescent cells with Nutlin-3A in LDLR−/− mice fed a HFD reduced expression of several SASP factors and senescent cell markers, MMP3, MMP13, PAI1, p21, IGFBP2, IL-1A, and IL-1B after one treatment cycle.

At the end of timepoint 2, LDLR−/− mice fed a HFD and treated with Nutlin-3A or vehicle (n=3 for all groups) were sacrificed, and aortic arches were dissected for RT-PCR analysis of SASP factors and senescent cell markers. Values were normalized to GAPDH and expressed as fold-change versus age-matched, vehicle-treated LDLR−/− mice on a normal diet. The data show expression of some SASP factors and senescent cell markers in the aortic arch within HFD mice. Clearance of senescent cells with multiple treatment cycles of Nutlin-3A in LDLR−/− mice fed a HFD reduced expression of most markers.

At the end of timepoint 3, LDLR−/− mice fed a HFD and treated with Nutlin-3A or vehicle (n=3 for all groups) were sacrificed, and aortas were dissected and stained with Sudan IV to detect the presence of lipid. Body composition of the mice was analyzed by MRI, and circulating blood cells were counted by Hemavet™.

FIG. 6 shows the results. Treatment with Nutlin-3A reduced the surface area covered by plaques in the descending aorta by about 45%. The platelet and lymphocyte counts were equivalent between the Nutlin-3A and vehicle treated mice. Treatment with Nutlin-3A also decreased mass and body fat composition in mice fed the high fat diet.

Example 8: Measuring Cytotoxicity for Cancer Cells In Vitro and In Vivo

The cellular activity of compounds can be evaluated in the interleukin-3 (IL-3)-dependent prolymphocytic FL5.12 murine cell line. Withdrawal of IL-3 induces FL5.12 apoptosis, by up-regulation of the proapoptotic factors Bim and Puma. Overexpression of Bcl-2 (FL5.12-Bcl-2) or Bcl-xL (FL5.12-Bcl-xL) protects against the effects of IL-3 withdrawal by sequestration of Bim and Puma. Compounds reverse the protection afforded by overexpression of Bcl-2 or Bcl-xL. Compounds are ineffective in eliciting cell death in the presence of IL-3 where FL5.12 cells are not subject to proapoptotic stimuli. The ability of compounds to kill FL5.12-Bcl-2 or FL5.12-Bcl-xL cells under IL-3 withdrawal can be attenuated in the presence of the caspase inhibitor ZVAD, indicating that cell killing is caspase dependent.

Co-immunoprecipitation studies can be done to determine if BH3 mimetic induced cytotoxicity can be attributed to the disruption of intracellular Bcl-2 family protein-protein interactions. Compounds induce a dose-dependent decrease in Bim:Bcl-xL interactions in FL5.12-Bcl-xL cells. Similar results are also observed for the disruption of Bim:Bcl-2 complexes in FL5.12-Bcl-2 cells indicating that compounds restore IL-3-dependent cell death by attenuating the ability of Bcl-xL and Bcl-2 to sequester proapoptotic factors such as Bim.

Testing of the ability of compounds listed in this disclosure to specifically kill cancer cells can be tested in similar assays using other established cell lines. These include HeLa cells, OVCAR-3, LNCaP, and any of the Authenticated Cancer Cell Lines available from Millipore Sigma, Burlington Mass., U.S.A. Compounds specifically kill cancer cells if they are lethal to the cells at a concentration that is at least 5-fold lower, and preferably 25- or 100-fold lower than a non-cancerous cell of the same tissue type. The control cell has morphologic features and cell surface markers similar to the cancer cell line being tested, but without signs of cancer.

In vivo, compounds are evaluated in flank xenograft models established from sensitive SCLC (H889) and hematologic (RS4;11) cell lines, or using other tumor-forming cancer cell lines, according to what type of cancer is of particular interest to the user. When dosed orally or intravenously, compounds induce rapid and complete tumor responses (CR) that are durable for several weeks after the end of treatment in all animals bearing H889 (SCLC) or RS4;11 (ALL) tumors. Similar treatment of mice bearing H146 SCLC tumors can induce rapid regressions in the animals.

Example 9: Synthesis

Compounds of this invention can be prepared by using or adapting the synthetic scheme shown in FIG. 1.

Example 10: Biochemical and Cellular Activity of Model Compounds

Compounds were assessed for inhibition of ligand binding to Bcl-2 in an in vitro assay. Compounds were assessed for inhibition of Bcl-xL activity in a direct binding assay according to the method described in Example 1, a homogeneous assay for determining inhibition of binding of a peptide ligand to the Bcl isoforms. The $EC_{50}$ values obtained for selected compounds are shown in TABLE 2A and TABLE 2B.

TABLE 2A

| Compound | Bcl-xL (nM) | Bcl-2 (nM) |
|---|---|---|
| NAAM 001 | 0.14 | 0.68 |
| NAAM 002 | 0.12 | 3.21 |
| NAAM 003 | 0.76 | 8.7 |
| NAAM 004 | 0.55 | 5.5 |
| NAAM 005 | 5.6 | 11.1 |

TABLE 2B

| Compound | IC50 Bcl-xL (nM) | IC50 Bcl-2 (nM) | IC50 Bcl-w (nM) |
|---|---|---|---|
| RJH01967 | 0.231 | 0.551 | 7.24 |
| RJH01325 | 0.067 | 3.089 | 3.32 |
| RJH01756 | 0.171 | 9.045 | 384 |
| RJH00601 | 0.174 | 10.71 | 9.6 |
| RJH01327 | 0.179 | 10.74 | 70.6 |
| RJH01819 | 0.029 | 72.7 | N/A |
| RJH01895 | 0.551 | 60.69 | >1000 |
| RJH00569 | 0.757 | 86.8 | N/A |
| RJH02289 | N/A | N/A | N/A |
| RJH02290 | N/A | N/A | N/A |

Compounds were assessed for senescent cell killing activity in human cells according to the method described in Examples 2 and 3. The cell lines were human bronchial epithelial (HBE) cells, small airway epithelial (SAE) cells, and human retinal microvascular endothelial (HRMEC) cells. Such cell types are available from the American Type Culture Collection (ATCC) under accession numbers CRL-2741, PCS-301-010, and PCS-1101-010, respectively.

$LD_{50}$ values obtained for selected compounds in the three different cell lines are shown in TABLE 3A and TABLE 3B.

TABLE 3A

| Compound | HBE (μM) | SAE (μM) | HRMEC (μM) |
|---|---|---|---|
| NAAM 001 | >10 | >10 | 0.12 |
| NAAM 002 | 1.2 | 2.7 | 0.76 |
| NAAM 003 | 0.43 | 0.56 | 1.3 |
| NAAM 004 | 2.4 | 0.96 | 0.35 |
| NAAM 005 | 0.85 | 1.5 | 0.29 |

TABLE 3B

| Compound | pEC50 HBE | pEC50 SAE | pEC50 HRMEC |
|---|---|---|---|
| RJH01967 | <5 | <5 | 6.97 |
| RJH01325 | 5.91 | 5.57 | 6.12 |
| RJH01756 | 6.37 | 6.25 | 6.41 |
| RJH00601 | 5.62 | 6.02 | 6.55 |
| RJH01327 | 6.07 | 5.83 | 6.53 |
| RJH01819 | <5 | <5 | N/A |
| RJH01895 | N/A | N/A | 5.08 |
| RJH00569 | N/A | N/A | N/A |
| RJH02289 | N/A | N/A | N/A |
| RJH02290 | N/A | N/A | N/A |

The several hypotheses presented in this disclosure provide a premise by way of which the reader may understand various aspects of the invention. This premise is provided for the intellectual enrichment of the reader. Practice of the invention does not require detailed understanding or application of the hypothesis. Except where stated otherwise, features of the hypothesis presented in this disclosure do not limit application or practice of the claimed invention.

For example, except where the elimination of senescent cells is explicitly required, the compounds may be used for treating the conditions described regardless of their effect on senescent cells. Although many of the senescence-related conditions referred to in this disclosure occur predominantly in older patients, the occurrence of senescent cells and the pathophysiology they mediate can result from other events, such as irradiation, other types of tissue damage, other types of disease, and genetic abnormalities. The invention may be practiced on patients of any age having the condition indicated, unless otherwise explicitly indicated or required.

Discussions about the mechanism of action of the compounds of the disclosure are also provided for the intellectual enrichment of the reader, and do not imply any limitation. Except where stated otherwise, the compounds may be used for removing senescent or cancer cells or for the treatment of disease conditions as claimed below, regardless of how they operate inside the target cells or in the treated subject.

Although the compounds and compositions referred to in this disclosure are illustrated in the context of eliminating senescent cells and treating senescence-associated conditions and cancer, compounds and their derivatives described herein that are novel can be prepared for any suitable purpose, including but not limited to laboratory use, the treatment of senescence-related conditions, as an automotive lubricant, and for diagnosis.

While the invention has been described with reference to the specific examples and illustrations, changes can be made and equivalents can be substituted to adapt to a particular context or intended use as a matter of routine development and optimization and within the purview of one of ordinary skill in the art, thereby achieving benefits of the invention without departing from the scope of what is claimed and their equivalents.

The invention claimed is:

1. A compound:

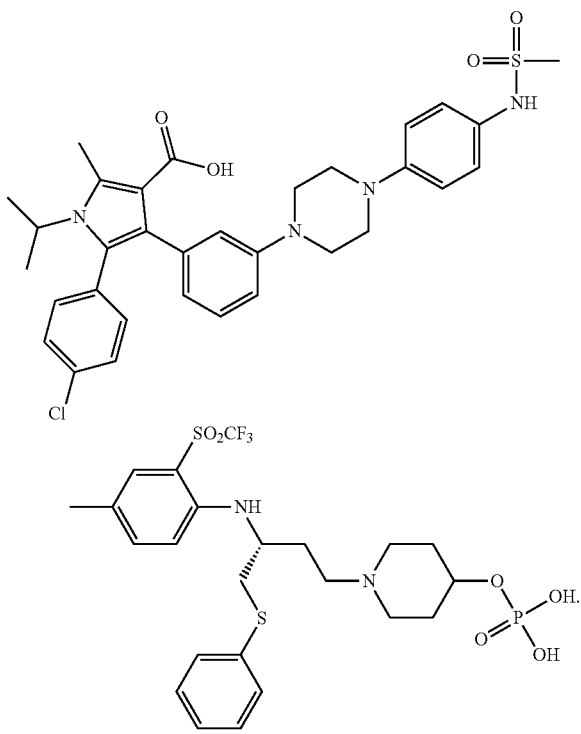

(R)-5-(4-chlorophenyl)-1-isopropyl-2-methyl-4-(3-(4-(4-(((1-(phenylthio)-4-(4-(phosphonooxy)piperidin-1-yl)butan-2-yl)amino)-3-(((trifluoromethyl)sulfonyl)phenyl)sulfonamido)phenyl)piperazin-1-yl)phenyl)-1H-pyrrole-3-carboxylic acid.

* * * * *